(12) United States Patent
Kandula

(10) Patent No.: US 11,555,007 B2
(45) Date of Patent: Jan. 17, 2023

(54) COMPOSITIONS AND METHODS FOR THE TREATMENT OF NEUROLOGICAL DISEASES

(71) Applicant: Cellix Bio Private Limited, Hyderabad (IN)

(72) Inventor: Mahesh Kandula, Andhra Pradesh (IN)

(73) Assignee: Cellix Bio Private Limited, Hydrabad (IN)

( * ) Notice: Subject to any disclaimer, the term of this patent is extended or adjusted under 35 U.S.C. 154(b) by 0 days.

(21) Appl. No.: 17/073,386

(22) Filed: Oct. 18, 2020

(65) Prior Publication Data
US 2021/0032194 A1 Feb. 4, 2021

Related U.S. Application Data

(63) Continuation of application No. PCT/IB2019/052391, filed on Mar. 25, 2019.

(30) Foreign Application Priority Data

Mar. 26, 2018 (IN) .............................. 201841011146

(51) Int. Cl.
  *C07C 225/28* (2006.01)
  *C07C 69/604* (2006.01)
(52) U.S. Cl.
  CPC .......... *C07C 225/28* (2013.01); *C07C 69/604* (2013.01)
(58) Field of Classification Search
  CPC .... C07C 225/28; C07C 69/204; C07C 69/604
  See application file for complete search history.

(56) References Cited

U.S. PATENT DOCUMENTS

| 6,248,789 B1 * | 6/2001 | Weg .................... A61K 31/135 |
| | | 424/435 |
| 9,066,865 B2 * | 6/2015 | Meyer ................. A61K 9/0046 |
| 2014/0178473 A1 | 6/2014 | Lim |
| 2016/0256415 A1 | 9/2016 | McCarty |

FOREIGN PATENT DOCUMENTS

| WO | WO2014057414 | * 4/2014 | ........... C07C 219/06 |
| WO | 2016205533 A1 | 12/2016 | |

OTHER PUBLICATIONS

Moller A. R, Sensorineural tinnitus: Its pathology and probable therapies, International Journal of Otolaryngology, Hindawi publishing corp., vol. 2016, Article ID 2830157,pp. 1-13 (Year: 2016).*
Zugno, A. I., et al., Omega-3 fatty acids prevent the ketamine-induced increase in acetycholinestease activity in an animal model of schizophrenia, Live Sciences, 121, pp. 65-69 (Year: 2015).*
PCT/IB2019/052391, "International Search Report", dated Mar. 10, 2019, 4 pages.

* cited by examiner

*Primary Examiner* — Yate' K Cutliff
(74) *Attorney, Agent, or Firm* — S. Elizabeth Miller, Esq.

(57) ABSTRACT

The invention relates to the compounds or its pharmaceutical acceptable polymorphs, solvates, enantiomers, stereoisomers and hydrates thereof. The pharmaceutical compositions comprising an effective amount of compounds of formula I, formula II and formula III and the methods for the treatment of neurological diseases may be formulated for oral, buccal, rectal, topical, transdermal, transmucosal, lozenge, spray, intravenous, oral solution, nasal spray, oral solution, suspension, oral spray, buccal mucosal layer tablet, parenteral administration, syrup, or injection. Such compositions may be used to treatment of neurological diseases.

21 Claims, No Drawings

COMPOSITIONS AND METHODS FOR THE TREATMENT OF NEUROLOGICAL DISEASES

PRIORITY

The present application is a continuation of International Patent Application No. PCT/IB2019/052391, filed Mar. 25, 2019, which claims the benefit of the Indian provisional Application No. 201841011146 filed on Mar. 26, 2018, the entire disclosures of which are relied on for all purposes and are incorporated into this application by reference.

FIELD OF THE INVENTION

This disclosure generally relates to compounds and compositions for the treatment of neurological diseases. More particularly, this invention relates to treating subjects with a pharmaceutically acceptable dose of compounds, crystals, solvates, enantiomer, stereoisomer, esters, hydrates, or mixtures thereof.

BACKGROUND OF THE INVENTION

Depression is one of the most devastating human conditions. In the Unites States alone, the economic burden attributed to major depressive disorder (MDD) increased by over 21% from 2005 to 2010; this cost is representative of the combination of direct effects, suicide-related expenditures and workplace costs. Several reasons may explain this sharp uptick in costs in a short period of time: an increase in both the population of the United States as well as in the prevalence of MDD; an increase in the costs of treatments; changes in the composition and quality of treatment services; and changes in the rates of employment and treatment-seeking behaviors. Without a doubt, the discovery of treatments to combat depression is essential.

Major depressive disorder (MDD) is a disabling illness that is associated with frequent relapses, incomplete recovery between episodes, and persistent psychosocial and functional impairment. MDD is considered one of the ten leading causes of disability worldwide and is also associated with an increased risk of suicidal behaviours. Although many psychopharmacological agents are currently available for the treatment of MDD, approximately 10-20% of patients treated with the common antidepressant medications do not achieve complete recovery and meet the criteria of treatment-resistance Good Rapid antidepressant effects of ketamine in MDD have been recognized for more than 15 years; in 2000, Berman et al conducted the first randomized, double-blind crossover study of intravenous ketamine (0.5 mg/kg) versus saline solution, in unipolar or bipolar patients in a major depressive episode. All 8 patients who were treated with ketamine had significant improvement in depressive symptoms, and 1 patient maintained mood improvement for 2-week postinfusion Managing acute pathology of often relies on the addressing underlying pathology and symptoms of the disease. There is currently a need in the art for new compositions to treatment or delay of the onset of neurological diseases and its associated complications progression.

SUMMARY OF THE INVENTION

The present invention provides compounds, compositions containing these compounds and methods for using the same to treat, prevent and/or ameliorate the effects of the conditions such as neurological diseases.

The invention herein provides compositions comprising of formula I or pharmaceutical acceptable hydrates or solvates thereof. The invention also provides pharmaceutical compositions comprising compound of formula I or intermediates thereof and one or more of pharmaceutically acceptable excipients and/or pharmaceutically acceptable carriers, including inert vehicles or diluents. These compositions may be used in the treatment of neurological diseases and its associated complications.

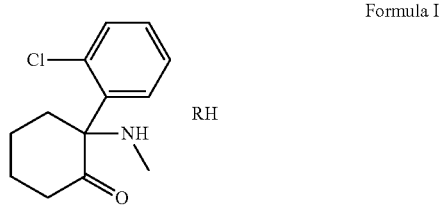

Formula I and pharmaceutically acceptable hydrates, solvates, prodrugs, enantiomers, and stereoisomers thereof;

wherein, RH represents caprylic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, phospholipids, phosphatidylcholine, oleic acid, elaidic acid, linoleic acid, linolenic acid, menthol, retinoic acid, vitamin A, retinol, linolelaidic acid, arachidonic acid, phospholipids, phosphatidylcholine, menthol, retinoic acid, vitamin a, retinol, retinal, isotretinoin, curcumin, tretinoin, α-carotene β-carotene retinol, d2 ergosterol, ergocalciferol, 7-dehydrocholesterol, cholecalciferol, 25-hydroxycholecalciferol, calcitriol (1,25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone (k1), menaquinones (k2), menadione (k3), menadiol (k4), thiamine, acefurtiamine, allithiamine, benfotiamine, fursultiamine, octotiamine, prosultiamine, sulbutiamine, riboflavin, niacin, nicotinamide, pantothenic acid, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, ascorbic acid, dehydroascorbic acid, 1-docosanol or

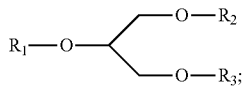

wherein, each of $R_1$, $R_2$ and $R_3$ independently represents

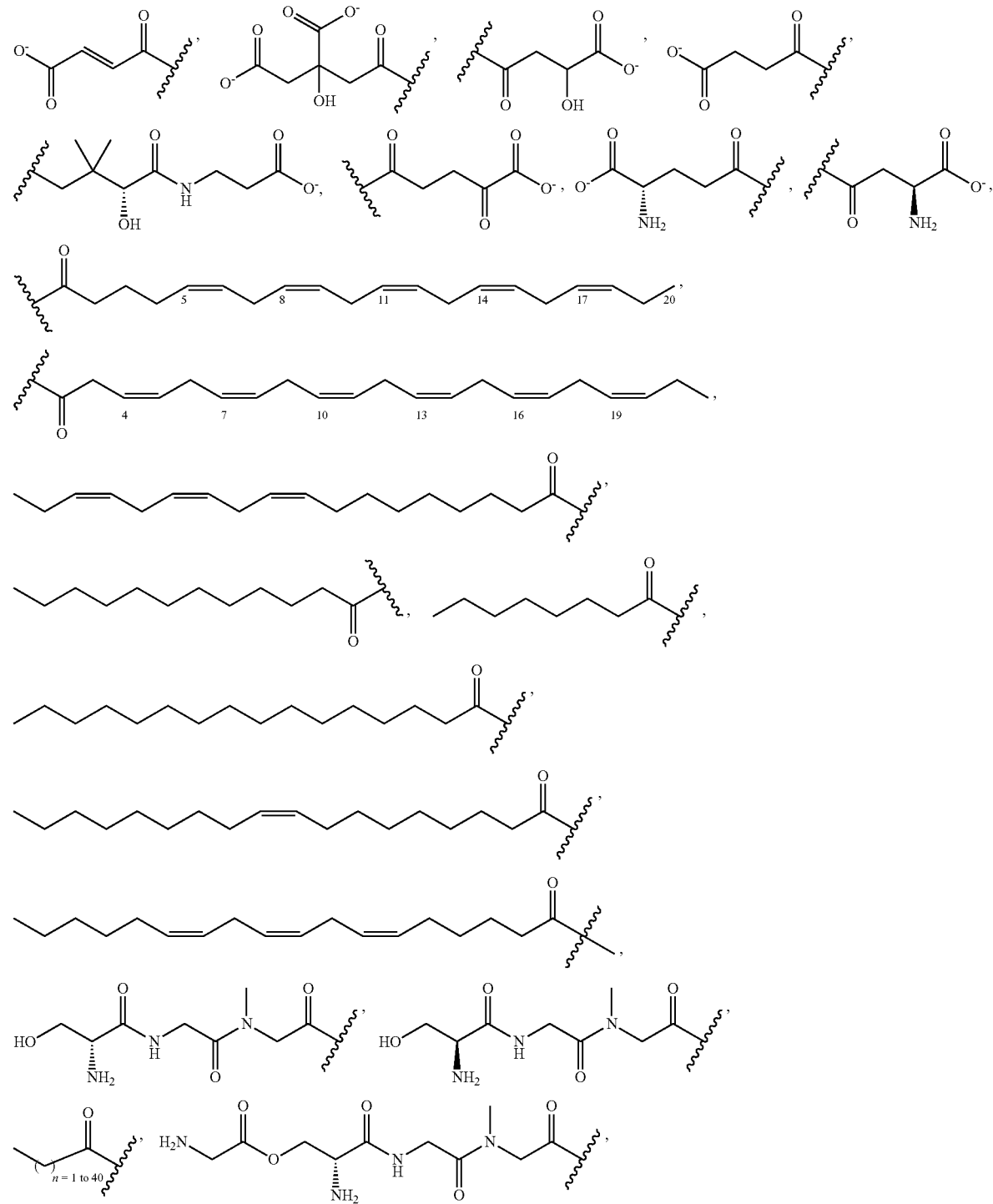

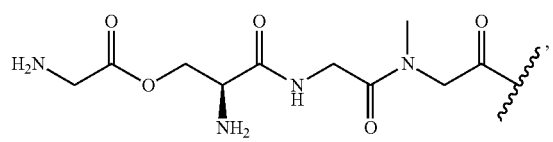

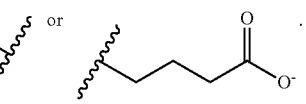

The compositions are typically compounds in the forms of hydrates or solvates of ketamine moiety and an acidic moiety [RH] containing compounds in which the ketamine is protonated and the acid moiety [RH] or the pharmaceutically acceptable salt thereof is at least in partially ionic form. In some instances, however, for example depending on the pH of the environment, the composition may be in the form of a mixture of ketamine and acid components [RH].

In the compound of formula I, ketamine moiety can exist as R enantiomer, S enantiomer or mixture thereof in equal proportions and one of the enantiomers could be selected for the salt preparation process or the racemic mixture containing equal propositions of R and S enantiomers can be selected for the salt preparation process. R-enantiomer is also referred as arketamine and S-enantiomer is also referred as esketamine.

In certain embodiments, the compounds of formula II are described:

Formula II

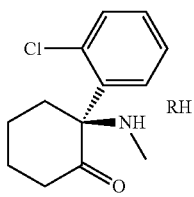

and pharmaceutically acceptable hydrates, solvates, prodrugs, enantiomers, and stereoisomers thereof;
wherein, RH represents
caprylic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, phospholipids, phosphatidylcholine, oleic acid, elaidic acid, linoleic acid, linolenic acid, menthol, retinoic acid, vitamin A, retinol, linolelaidic acid, arachidonic acid, phospholipids, phosphatidylcholine, menthol, retinoic acid, vitamin a, retinol, retinal, isotretinoin, curcumin, tretinoin, α-carotene β-carotene retinol, d2 ergosterol, ergocalciferol, 7-dehydrocholesterol, cholecalciferol, 25-hydroxycholecalciferol, calcitriol (1,25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone (k1), menaquinones (k2), menadione (k3), menadiol (k4), thiamine, acefurtiamine, allithiamine, benfotiamine, fursultiamine, octotiamine, prosultiamine, sulbutiamine, riboflavin, niacin, nicotinamide, pantothenic acid, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, ascorbic acid, dehydroascorbic acid, 1-docosanol or

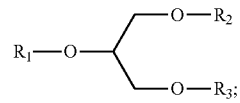

wherein, each of $R_1$, $R_2$ and $R_3$ independently represents

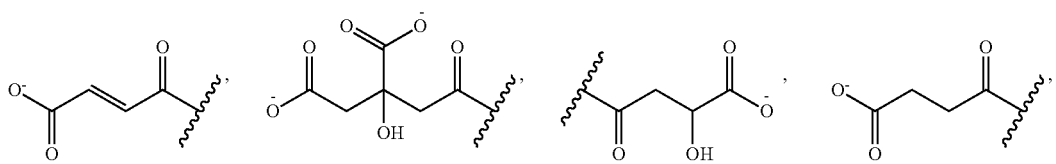

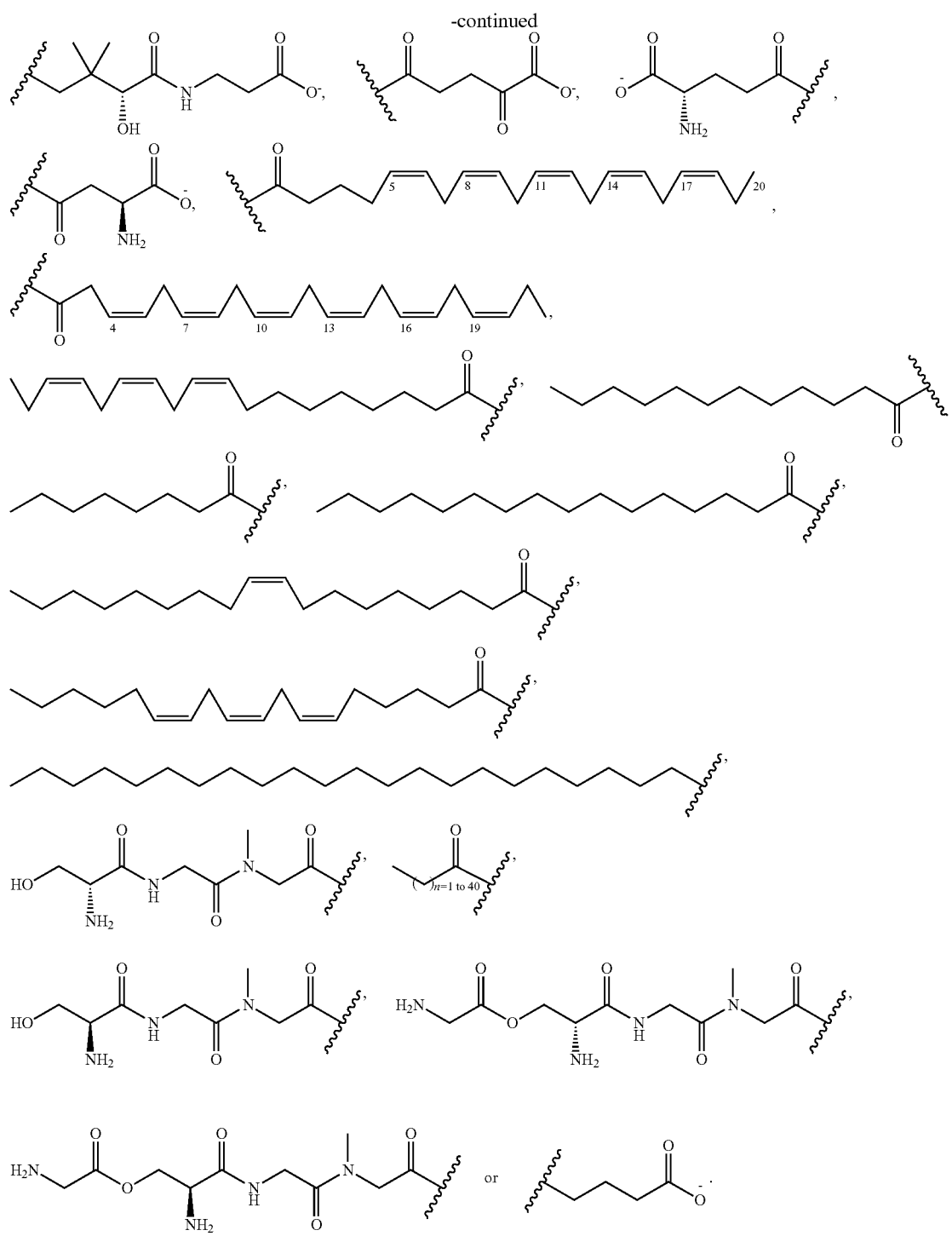

The compositions are typically compounds in the forms of hydrates or solvates of an S-enantiomer of the ketamine also known as esketamine and an acidic moiety [RH] containing compounds in which, the esketamine is protonated and the acid moiety [RH] or the pharmaceutically acceptable salt thereof is at least in partially ionic form. In some instances, however, for example depending on the pH of the environment, the composition may be in the form of a mixture of esketamine and acid components [RH].

In certain embodiments, the compounds of formula III are described:

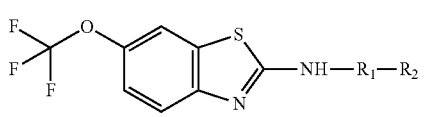

Formula III and pharmaceutically acceptable hydrates, solvates, enantiomers, and stereoisomers thereof;
wherein,
R₁ represents null,
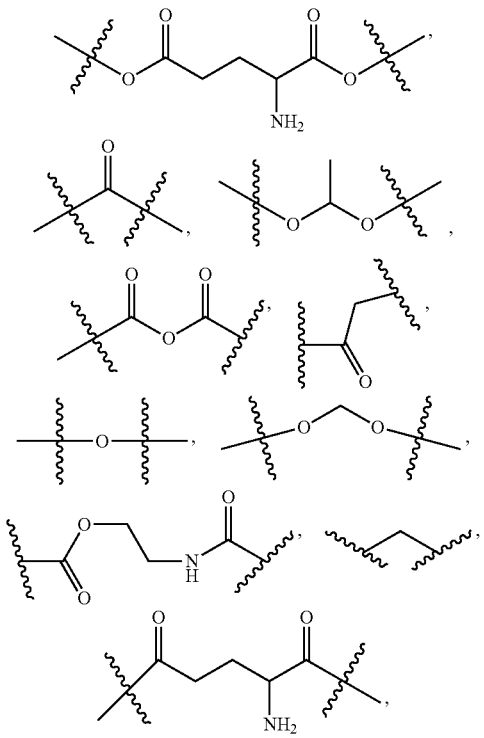
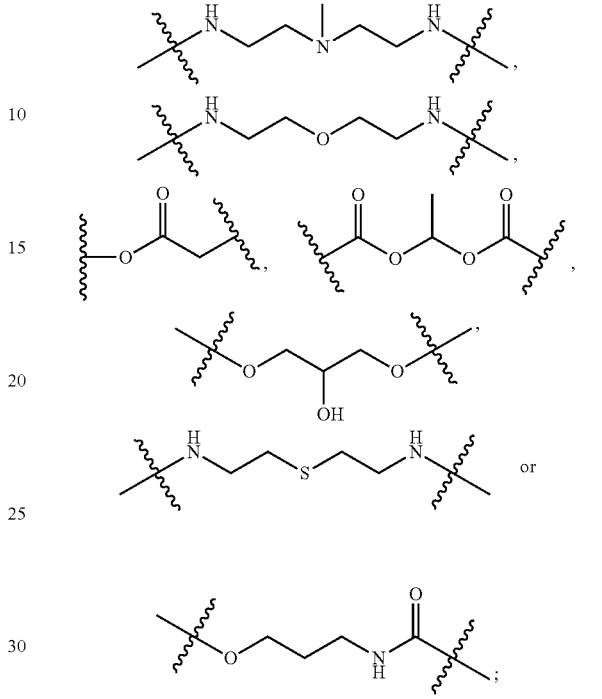
R₂ represents
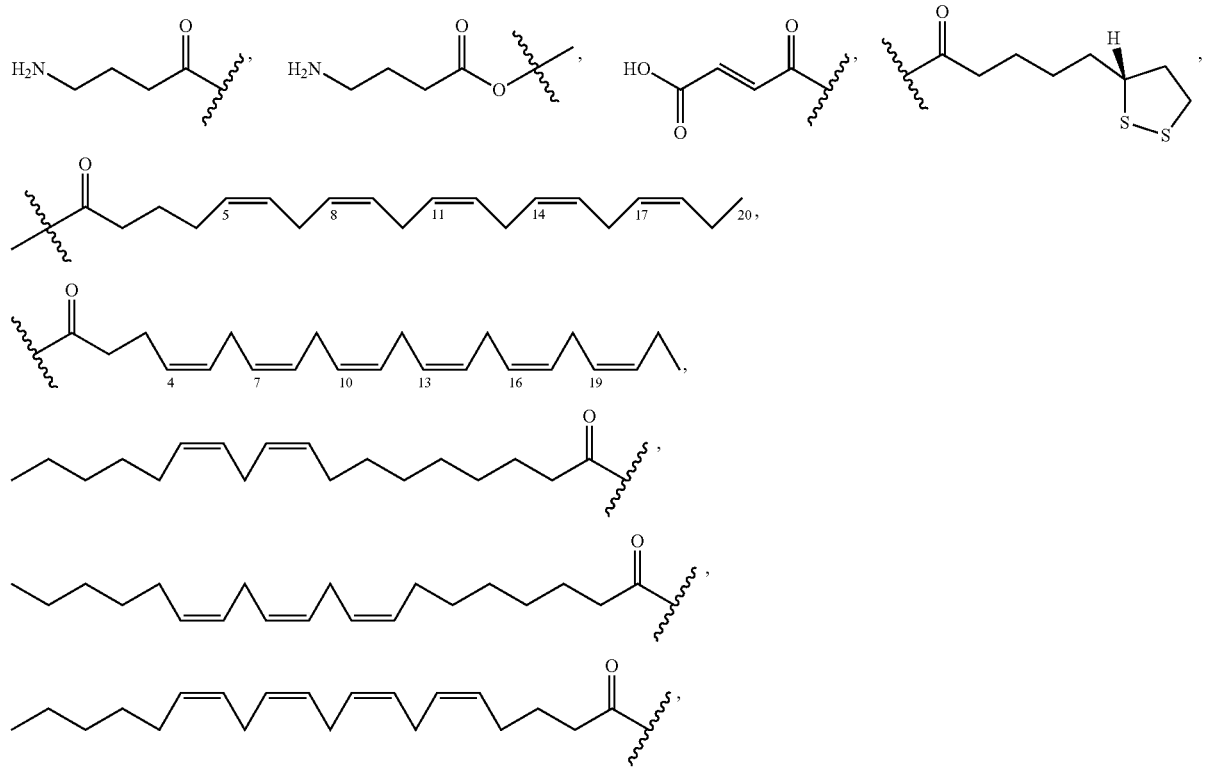

-continued

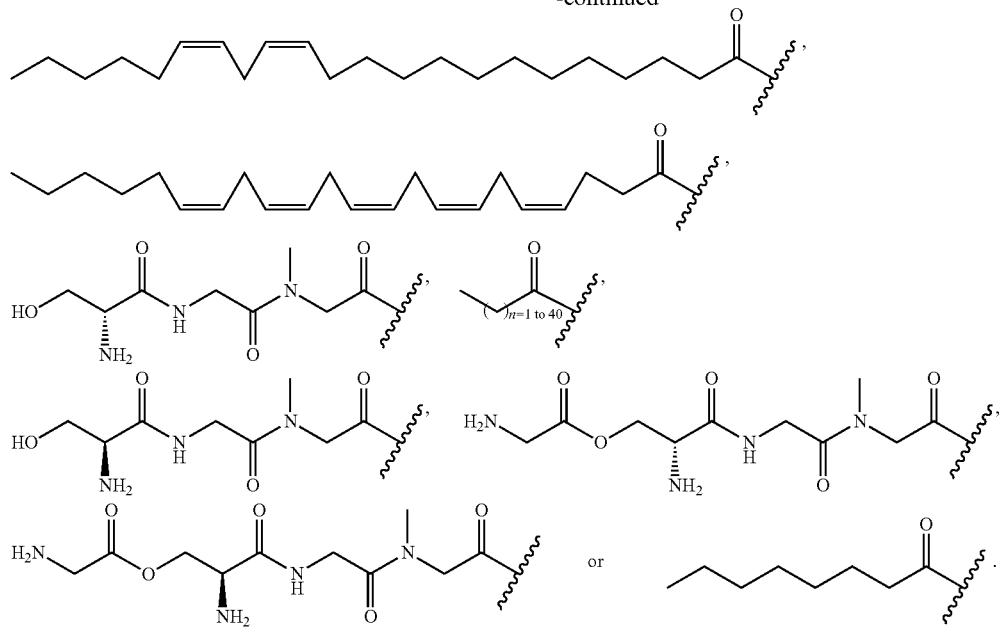

The invention also provides pharmaceutical compositions comprising compositions of formula I as an active ingredient in a therapeutically effective amount and pharmaceutically acceptable excipients.

The invention also provides pharmaceutical compositions comprising compositions of formula II as an active ingredient in a therapeutically effective amount and pharmaceutically acceptable excipients.

The invention also provides pharmaceutical compositions comprising compositions of formula III as an active ingredient in a therapeutically effective amount and pharmaceutically acceptable excipients.

The application also discloses a pharmaceutical composition comprising the compound of formula I, formula II, or formula II and pharmaceutically acceptable excipients. The pharmaceutical composition can be formulated as an oral dosage form, systemic dosage form, topical dosage form, spray, parenteral dosage form, subdermal dosage form, or transdermal dosage form.

The application also discloses a pharmaceutical composition comprising the compound of formula I and pharmaceutically acceptable excipients. In some aspects, the pharmaceutical composition comprising compound of formula I is formulated as dosage form selected from oral spray, nasal spray, transdermal patch, tablet, sublingual tablet, mucoadhesive spray, mucoadhesive tablet, lozenge, nasal inhaler, injection, autoinjector subdermal or intramuscular, suspension, or oral solution for systemic administration, oral administration, sustained release, parenteral administration, intravenous administration, subdermal administration, or transdermal administration. In some aspect the dosage form comprises the pharmaceutical composition and pharmaceutically acceptable suitable carrier.

The application also discloses a pharmaceutical composition comprising the compound of formula II and pharmaceutically acceptable excipients. In some aspects, the pharmaceutical composition comprising compound of formula II is formulated as dosage form selected from oral spray, nasal spray, transdermal patch, tablet, sublingual tablet, mucoadhesive spray, mucoadhesive tablet, lozenge, nasal inhaler, injection, autoinjector subdermal or intramuscular, suspension, or oral solution for systemic administration, oral administration, sustained release, parenteral administration, intravenous administration, subdermal administration, or transdermal administration. In some aspect the dosage form comprises the pharmaceutical composition and pharmaceutically acceptable suitable carrier.

The application in some aspect discloses a pharmaceutical composition comprising the compound of formula III and pharmaceutically acceptable excipients. In some aspects, the pharmaceutical composition comprising compound of formula III is formulated as dosage form selected from oral spray, nasal spray, transdermal patch, tablet, sublingual tablet, mucoadhesive spray, mucoadhesive tablet, lozenge, nasal inhaler, injection, autoinjector subdermal or intramuscular, suspension, or oral solution for systemic administration, oral administration, sustained release, parenteral administration, intravenous administration, subdermal administration, or transdermal administration. In some aspect the dosage form comprises the pharmaceutical composition and pharmaceutically acceptable suitable carrier.

The compositions described herein have several uses. The present application provides, for example, methods of treating a patient suffering from neurological diseases or its related complications manifested from metabolic or genetic conditions or disorders, metabolic diseases, chronic diseases or disorders; neurodegenerative disorders, metabolic condition, Hepatology, Cancer, Respiratory, Hematological, Orthopedic, Cardiovascular, Renal, Skin, Vascular or Ocular complications by administering administering to a subject the compound of formula I, formula II, or formula III s an active ingredient in a therapeutically effective amount or pharmaceutical composition comprising the same.

Herein the application also provides a kit comprising any of the pharmaceutical compositions disclosed herein. The kit may comprise instructions for use in the treatment of neurological diseases or its related complications.

DETAILED DESCRIPTION OF THE INVENTION

Definitions

As used herein, the following terms and phrases shall have the meanings set forth below. Unless defined otherwise, all technical and scientific terms used herein have the same meaning as commonly understood to one of ordinary skill in the art.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "metabolic condition" refers to an Inborn errors of metabolism (or genetic metabolic conditions) are genetic disorders that result from a defect in one or more metabolic pathways; specifically, the function of an enzyme is affected and is either deficient or completely absent.

The term "polymorph" as used herein is art-recognized and refers to one crystal structure of a given compound.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable excipient" is art-recognized. The Pharmaceutical excipients are substances other than the active pharmaceutical ingredient (API) that are intentionally included to do functions like: aid in the processing of the drug delivery system during its manufacture; protect, support, or enhance the stability, bioavailability, or acceptability of the product to patients; assist in product identification; enhance any attribute of the overall safety; assist in the effectiveness and/or delivery of the drug; and assist in maintaining the integrity of the drug product during storage. Pharmaceutically acceptable excipient include for example a stabilizer, an inert carrier, a vehicle, a diluent, a surfactant, a filler, a humectant, an adsorbent, an antiadherent, a binder, a lubricant, a glidant, a super disintegrant, a disintegrant, a preservative, an antioxidant, a solution retarding agent, an absorption accelerator, a wetting agent, an absorbent, a coloring agent, a flavoring agent, a sorbent, a coating agent, a sweetener, a buffering agent, a propellant, or the like and mixtures thereof.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "predicting" as used herein refers to assessing the probability related diseases patient will suffer from abnormalities or complication and/or terminal platelet aggregation or failure and/or death (i.e. mortality) within a defined time window (predictive window) in the future. The mortality may be caused by the central nervous system or complication. The predictive window is an interval in which the subject will develop one or more of the said complications according to the predicted probability. The predictive window may be the entire remaining lifespan of the subject upon analysis by the method of the present invention.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating neurological diseases, depression, physiological disorders, psychiatric diseases, OCD, ALS, Alzehimer's disease, autism, neurodegenerative diseases, major depressive disorder and other related diseases or any other medical condition, is well understood in the art, and includes administration of a composition which reduces the frequency of, or delays the onset of, symptoms of a medical condition in a subject relative to a subject which does not receive the composition.

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular solvate or hydrate or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the subject compositions provided herein may be determined by reference to the plasma concentrations of the therapeutic composition or other encapsulated materials. For example, the maximum plasma concentration (Cmax) and the area under the plasma concentration-time curve from time 0 to infinity may be used.

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active solvate or hydrate and/or composition, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of a solvate or hydrate or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The present disclosure also contemplates prodrugs of the compositions disclosed herein, as well as pharmaceutically acceptable hydrates or solvates of said prodrugs.

This application discloses a pharmaceutical composition comprising a pharmaceutically acceptable excipient and/or carrier and the composition of a compound of formula I, formula II or formula III that may be formulated for systemic or topical or oral administration. The pharmaceutical composition may be also formulated for oral administration, oral solution, injection, subdermal administration, or transdermal administration. The pharmaceutical composition may further comprise at least one of a pharmaceutically acceptable excipient selected from a stabilizer, a carrier, a vehicle, a diluent, a surfactant, a filler, a humectant, an adsorbent, an antiadherent, a binder, a lubricant, a glidant, a super disintegrant, a disintegrant, a preservative, an antioxidant, a solution retarding agent, an absorption accelerator, a wetting agent, an absorbent, a coloring agent, a flavoring agent, a sorbent, a coating agent, a sweetener, a buffering agent, a propellant, or the like and mixtures thereof.

This application discloses the pharmaceutical composition comprising the compound of formula I, formula II, or formula III as an active ingredient in a therapeutically effective amount; and a pharmaceutically acceptable excipient, wherein the pharmaceutical composition is formulated as an oral dosage form, systemic dosage form, topical dosage form, spray, parenteral dosage form, subdermal dosage form, or transdermal dosage form.

This application discloses the pharmaceutical composition formulated in a unit dosage form selected from the group consisting of tablet, sublingual tablet, mucoadhesive tablet, multilayer tablet, capsule, capsules containing tablet, controlled-release form, sustained-release form, suppository, tampons, pessaries, pill, lozenge, powder, beads, granule, nanoparticles, beads or granules in solid or liquid forms, oral spray, nasal spray, mucoadhesive spray, intra nasal spray, foam, nasal inhaler, liquid solution, syrups, elixirs, emulsions, microemulsions, subdermal autoinjector, intramuscular autoinjector, injection, stereotactic injection, liquid suspension, intravenous suspension, sterile parenteral solution, sterile parenteral suspension, sterile non-parenteral solution, sterile non-parenteral suspension, topical ointment, topical paste, topical cream, topical lotion, topical gel, and transdermal patch.

In many embodiments, the pharmaceutical compositions described herein will incorporate the disclosed compounds or compositions of formula I or formula II or formula III to be delivered in an amount sufficient to a patient in a therapeutically effective amount of a compound of formula I, formula II or formula III or composition as part of a prophylactic or therapeutic treatment. The desired concentration of compound of formula I, formula II or formula III or its pharmaceutical acceptable hydrates or solvates will depend on absorption, inactivation, and excretion rates of the drug as well as the delivery rate of the hydrates or solvates and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of formula I, formula II or formula III may be adjusted to accommodate variations in the treatment parameters. Such treatment parameters include the clinical use to which the preparation is put, e.g., the site treated, the type of patient, e.g., human or non-human, adult or child, and the nature of the disease or condition.

The concentration and/or amount of any compound of formula I, formula II or formula III may be readily identified by routine screening in animals, e.g., rats, by screening a range of concentration and/or amounts of the material in question using appropriate assays. Known methods are also available to assay local tissue concentrations, diffusion rates of the hydrates or solvates or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with formula I, formula II or formula III such as those disclosed herein are injected adjacent to the loop, released drugs are collected in the dialysate in proportion to their local tissue concentrations. The progress of diffusion of the hydrates or solvates or compositions may be determined thereby with suitable calibration procedures using known concentrations of hydrates or solvates or compositions.

In certain embodiments, the dosage of the subject compounds of formula I, formula II or formula III provided herein may be determined by reference to the plasma concentrations of the therapeutic composition or other encapsulated materials. For example, the maximum plasma concentration (Cmax) and the area under the plasma concentration-time curve from time 0 to infinity may be used.

In an embodiment, the present disclosure also discloses a method of the treatment, prevention or amelioration of a neurological diseases or an associated complication comprising administering to a subject the compound of formula I, formula II or formula III as an active ingredient in a therapeutically effective amount, or the pharmaceutical composition comprising the same. The the associated complication can be depression, treatment resistant depression, chronic pain, neurological diseases or combinations thereof.

Generally, in carrying out the methods detailed in this application, an effective dosage for the compounds of formula I, formula II or formula III is in the range of about 0.01 mg/kg/day to about 100 mg/kg/day in single or divided doses, for instance 0.01 mg/kg/day to about 50 mg/kg/day in single or divided doses. The compounds of formula I, formula II or formula III may be administered to a subject at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compounds of formula I, formula II or formula III may also be administered to a human patient at a dose of, for example, between 0.1 mg and 1000 mg, between 5 mg and 80 mg, or less than 1.0, 9.0, 12.0, 20.0, 50.0, 75.0, 100, 300, 400, 500, 800, 1000, 2000, 5000 mg per day. In certain embodiments, the compositions herein are administered at an amount that is less than 95%, 90%, 80%, 70%, 60%, 50%, 40%, 30%, 20%, or 10% of the compound of formula I, formula II or formula III required for the same therapeutic benefit.

An effective amount of the compound of formula I, formula II or formula III described herein refers to the amount of one of said hydrates or solvates or compositions which is capable of inhibiting or preventing a disease.

An effective amount may be sufficient to prohibit, treat, alleviate, ameliorate, halt, restrain, slow or reverse the progression, or reduce the severity of a complication resulting from nerve damage or demyelization and/or elevated reactive oxidative-nitrosative species and/or abnormalities in neurotransmitter homeostasis's, in patients who are at risk for such complications. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

The compositions provided by this application may be administered to a subject in need of treatment by a variety of conventional routes of administration, including orally, topically, parenterally, e.g., intravenously, subcutaneously or intramedullary. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions can be formulated by combining the compositions and the pharmaceutically acceptable excipient and/or carriers, vehicles or diluents to be readily administered in a variety of dosage forms such as tablets, powders, lozenges, syrups, injectable solutions and the like. These pharmaceutical compositions can, if desired, comprise additional ingredients such as flavorings, binders, excipients, and the like. Thus, for purposes of oral administration, tablets containing various excipients such as L-arginine, sodium citrate, calcium carbonate and calcium phosphate may be employed along with various disintegrates such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. The compounds of formula I, formula II or formula III may also comprise enterically coated comprising of various excipients, as is well known in the pharmaceutical art.

For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may comprise e.g. 10 to 100, 50 to 250, 150 to 500 mg, or 350 to 800 mg e.g. 10, 50, 100, 300, 500, 700, 800 mg of the compounds of formula I, formula II or formula III disclosed herein, for instance, compounds of formula I, formula II or formula III or pharmaceutical acceptable hydrates or solvates of a compounds of formula I or formula II, or formula III.

Generally, a composition as described herein may be administered orally; or parenterally including intravenous, intramuscular, subcutaneous or intramedullary route. Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the neurological disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of subject body weight.

Expressed in terms of concentration, an active ingredient of the present invention can be presented in the pharmaceutical compositions for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The pharmaceutical compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. For oral administration either solid or fluid unit dosage forms can be prepared.

As discussed above, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their hydrates or solvates, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their hydrates or solvates, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate hydrates or solvates, and mixtures thereof. Examples of preservatives include, but are not limited to, citric acid, tartaric acid, lactic acid, malic acid, acetic acid, benzoic acid, and sorbic acid, and mixtures thereof.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Extended release formulations are generally prepared as diffusion or osmotic systems, for example, as described in "Remington—The Science and Practice of Pharmacy", 20th. Ed., Lippincott Williams & Wilkins, Baltimore, Md., 2000). A diffusion system typically consists of one of two types of devices, reservoir and matrix, which are wellknown and described in die art. The matrix devices are generally prepared by compressing the drug with a slowly dissolving polymer carrier into a tablet form.

An immediate release portion can be added to the extended release system by means of either applying an immediate release layer on top of the extended release core; using coating or compression processes or in a multiple unit system such as a capsule containing extended and immediate release beads.

Delayed release dosage formulations are created by coating a solid dosage form with a film of a polymer which is insoluble in the acid environment of the stomach, but soluble in the neutral environment of small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains a therapeutically effective amount of active agent. In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 3.0 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of one or more compounds of formula I, formula II or formula III or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

Methods of preparing these formulations or compositions include the step of bringing into association subject compositions that is a certain amount of compound of formula I, formula II or formula III with a pharmaceutically acceptable carrier and, optionally, one or more accessory ingredients. In general, the formulations are prepared by uniformly and intimately bringing into association a subject composition with liquid carriers, or finely divided solid carriers, or both, and then, if necessary, shaping the product.

The compounds of formula I, formula II or formula III described herein or the pharmaceutical compositions comprising the same may be formulated and administered in the form of an inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

In solid dosage forms for oral administration selected from but not limiting to capsules, tablets, pills, dragees, powders, granules and the like, the subject composition, that is the compound of formula I, formula II, or formula III in therapeutically effective amount, is mixed with one or more pharmaceutically acceptable carriers and/or any of the following pharmaceutically acceptable excipient: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid dosage form in soft and hard-filled gelatin capsules may be formulated using fillers for example lactose or milk sugars, as well as high molecular weight polyethylene glycols and the like.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils for example cottonseed, corn, peanut, sunflower, soybean, olive, castor, and sesame oils, glycerol, tetrahydrofuryl alcohol, polyethylene glycols and fatty acid esters of sorbitan, and mixtures thereof.

Suspensions, in addition to the subject compositions, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with pharmaceutically acceptable other excipients selected from any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Methods of delivering a pharmaceutical composition or compositions via a transdermal patch are known in the art. Exemplary patches and methods of patch delivery are described in U.S. Pat. Nos. 6,974,588, 6,564,093, 6,312,716, 6,440,454, 6,267,983, 6,239,180, and 6,103,275.

In another embodiment, a transdermal patch may comprise: a substrate sheet comprising a composite film formed of a resin composition comprising 100 parts by weight of a polyvinyl chloride-polyurethane composite and 2-10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer. A method for the manufacture of the above-mentioned substrate sheet comprises preparing the above resin composition molding the resin composition into a composite film by a calendar process, and then adhering a polyalkylene terephthalate film on one side of the composite film by means of an adhesive layer thereby forming the substrate sheet, and forming a primer layer comprising a saturated polyester resin on the outer surface of the polyalkylene terephthalate film.

Another type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

Transdermal patches may be passive or active. Passive transdermal drug delivery systems currently available, such as the nicotine, estrogen and nitroglycerine patches, or may be delivered using technology such as electrical assist (iontophoresis).

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

Also disclosed is a kit comprising the compound of formula I, formula II, or formula III as an active ingredient in a therapeutically effective amount, or a pharmaceutical composition as described herein, and an instruction for use in the treatment of neurological diseases and associated complications.

In certain embodiments, compounds of formula (I) are disclosed:

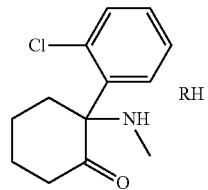

Formula I and pharmaceutically acceptable hydrates, solvates, prodrugs, enantiomers, and stereoisomers thereof;
wherein, RH represents
caprylic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, phospholipids, phosphatidylcholine, oleic acid, elaidic acid, linoleic acid, linolenic acid, menthol, retinoic acid, vitamin A, retinol, linolelaidic acid, arachidonic acid, phospholipids, phosphatidylcholine, menthol, retinoic acid, vitamin a, retinol, retinal, isotretinoin, curcumin, tretinoin, α-carotene β-carotene retinol, d2 ergosterol, ergocalciferol, 7-dehydrocholesterol, cholecalciferol, 25-hydroxycholecalciferol, calcitriol (1, 25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone (k1), menaquinones (k2), menadione (k3), menadiol (k4), thiamine, acefurtiamine, allithiamine, benfotiamine, fursultiamine, octotiamine, prosultiamine, sulbutiamine, riboflavin, niacin, nicotinamide, pantothenic acid, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, ascorbic acid, dehydroascorbic acid, 1-docosanol or

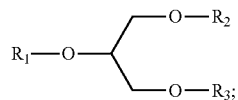

wherein, each of $R_1$, $R_2$ and $R_3$ independently represents

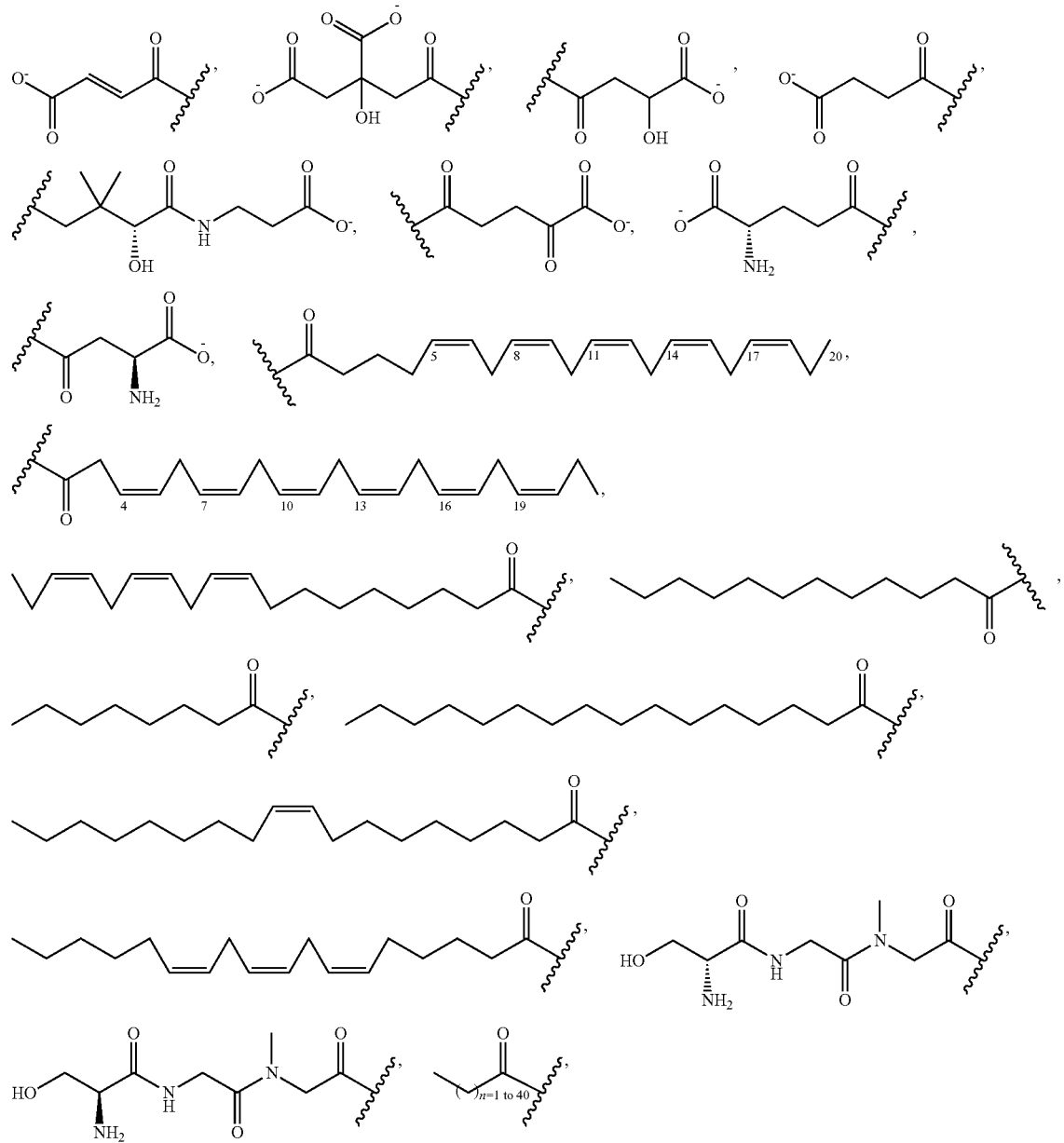

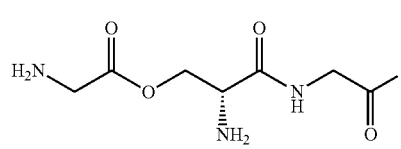
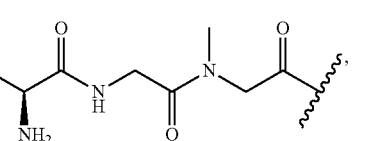

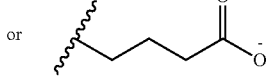 or 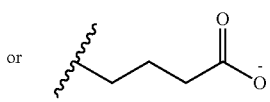

The compound is in the form of hydrate or solvate of ketamine moiety and an acidic moiety [RH] containing compound in which the ketamine is protonated and the acid moiety [RH] or the pharmaceutically acceptable salt thereof is at least in partially ionic form. In some instances, however, for example depending on the pH of the environment, the compound may be in the form of a mixture of ketamine and acid components [RH].

In the compound of formula I, ketamine moiety can exist as R enantiomer, S enantiomer or mixture thereof in equal proportions and one of the enantiomer could be selected for the salt preparation process or the racemic mixture containing equal propositions of R and S enantiomers can be selected for the salt preparation process. R-enantiomer is also referred as arketamine and S-enantiomer is also referred as esketamine.

In certain embodiments, compounds of formula II are disclosed:

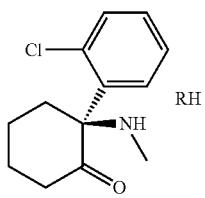

Formula II and pharmaceutically acceptable hydrates, solvates, prodrugs, enantiomers, and stereoisomers thereof;
wherein, RH represents
caprylic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, undecylenic acid, omega 3 fatty acids, omega 6 fatty acids, n-acetyl cysteine (nac), furoate, methyl furoate, ethyl furoate, aminocaproic acid, caproic acid, caprilic acid, capric acid, lauric acid, alpha lipoic acid, R-lipoic acid, myristic acid, myristoleic acid, palmitic acid, palmitoleic acid, phospholipids, phosphatidylcholine, oleic acid, elaidic acid, linoleic acid, linolenic acid, menthol, retinoic acid, vitamin A, retinol, linolelaidic acid, arachidonic acid, phospholipids, phosphatidylcholine, menthol, retinoic acid, vitamin a, retinol, retinal, isotretinoin, curcumin, tretinoin, α-carotene β-carotene retinol, d2 ergosterol, ergocalciferol, 7-dehydrocholesterol, cholecalciferol, 25-hydroxycholecalciferol, calcitriol (1,25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone (k1), menaquinones (k2), menadione (k3), menadiol (k4), thiamine, acefurtiamine, allithiamine, benfotiamine, fursultiamine, octotiamine, prosultiamine, sulbutiamine, riboflavin, niacin, nicotinamide, pantothenic acid, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, ascorbic acid, dehydroascorbic acid, 1-docosanol or

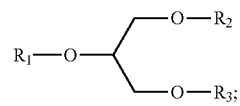

wherein, each of $R_1$, $R_2$ and $R_3$ independently represents

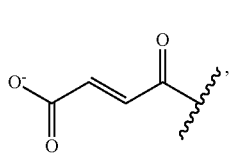 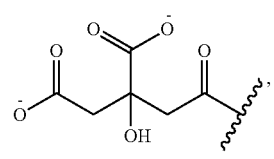 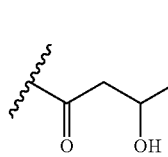 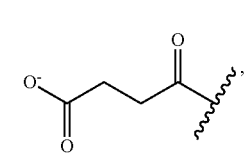

-continued

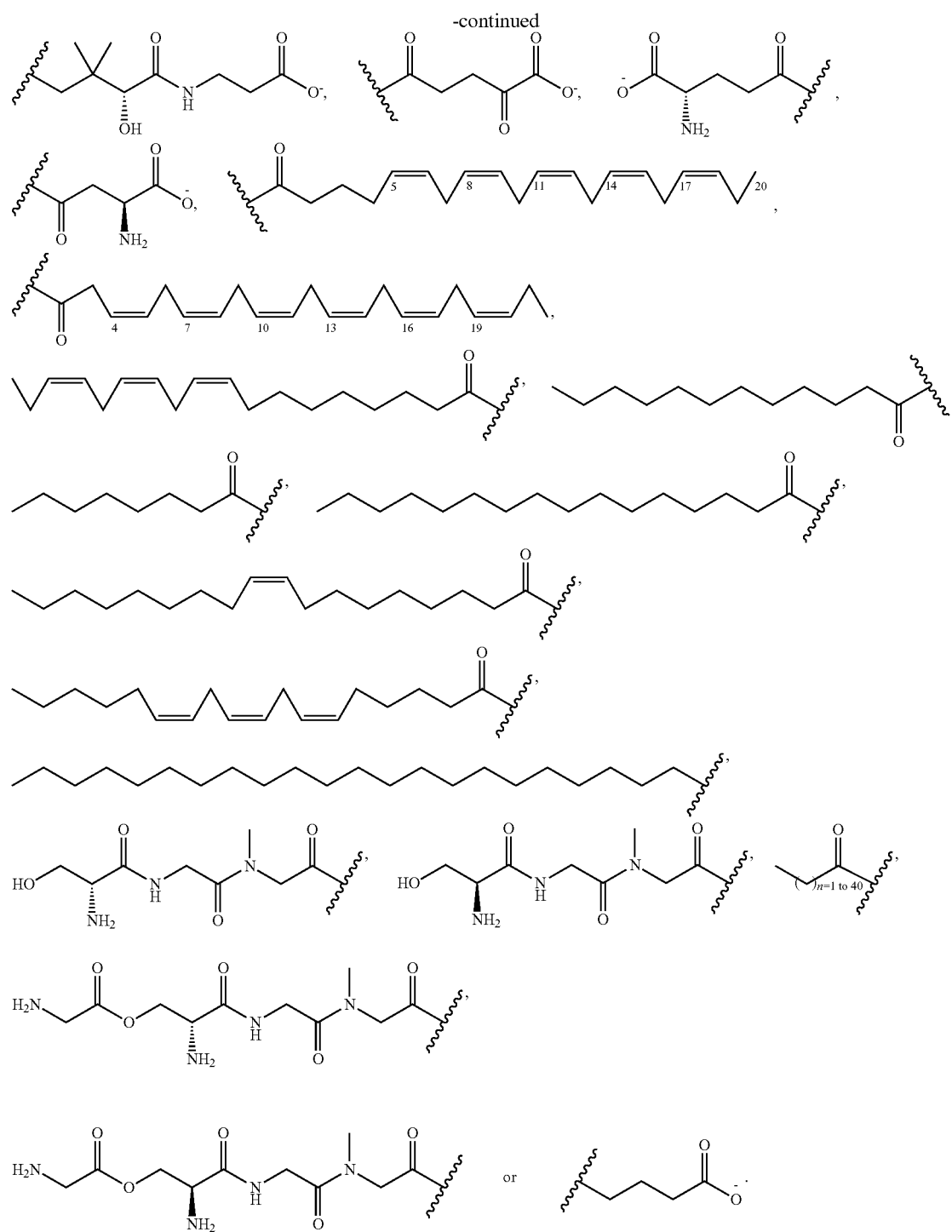

The compound in the form of hydrate or solvate of an S-enantiomer of the ketamine also known as esketamine and an acidic moiety [RH] containing compound in which, the esketamine is protonated and the acid moiety [RH] or the pharmaceutically acceptable salt thereof is at least in partially ionic form. In some instances, however, for example depending on the pH of the environment, the compound may be in the form of a mixture of esketamine and acid components [RH].

In certain embodiments, the compounds of formula III are described:

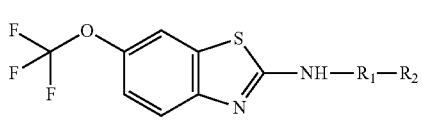

Formula III and pharmaceutically acceptable hydrates, solvates, enantiomers, and stereoisomers thereof;
wherein, $R_1$ represents null,
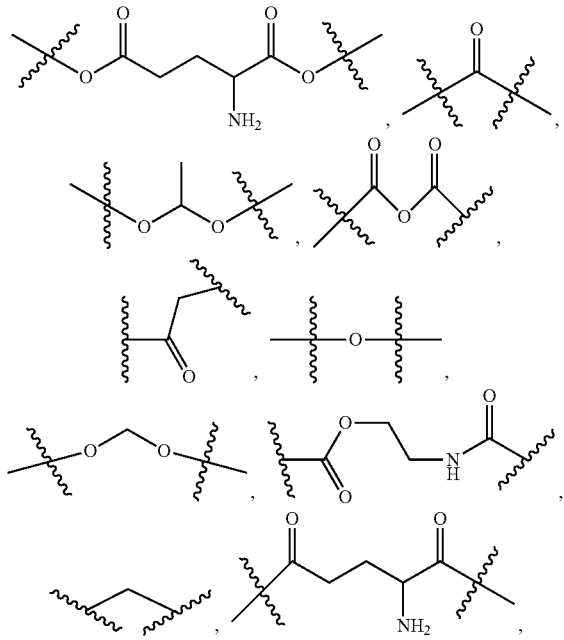
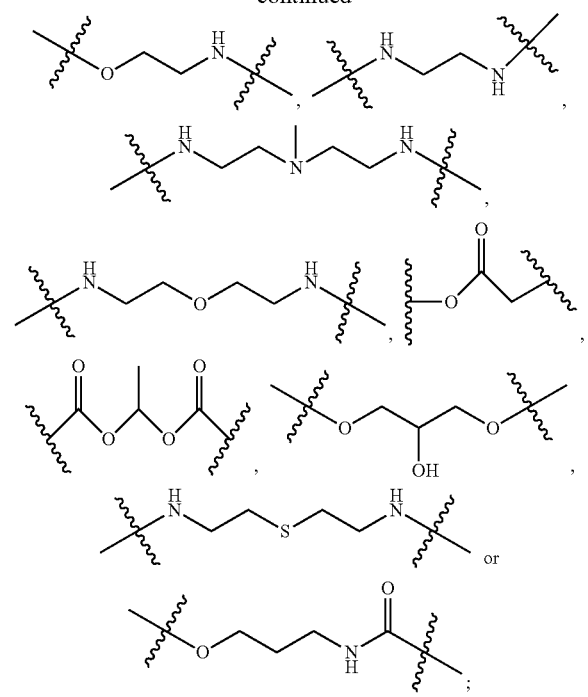
$R_2$ represents
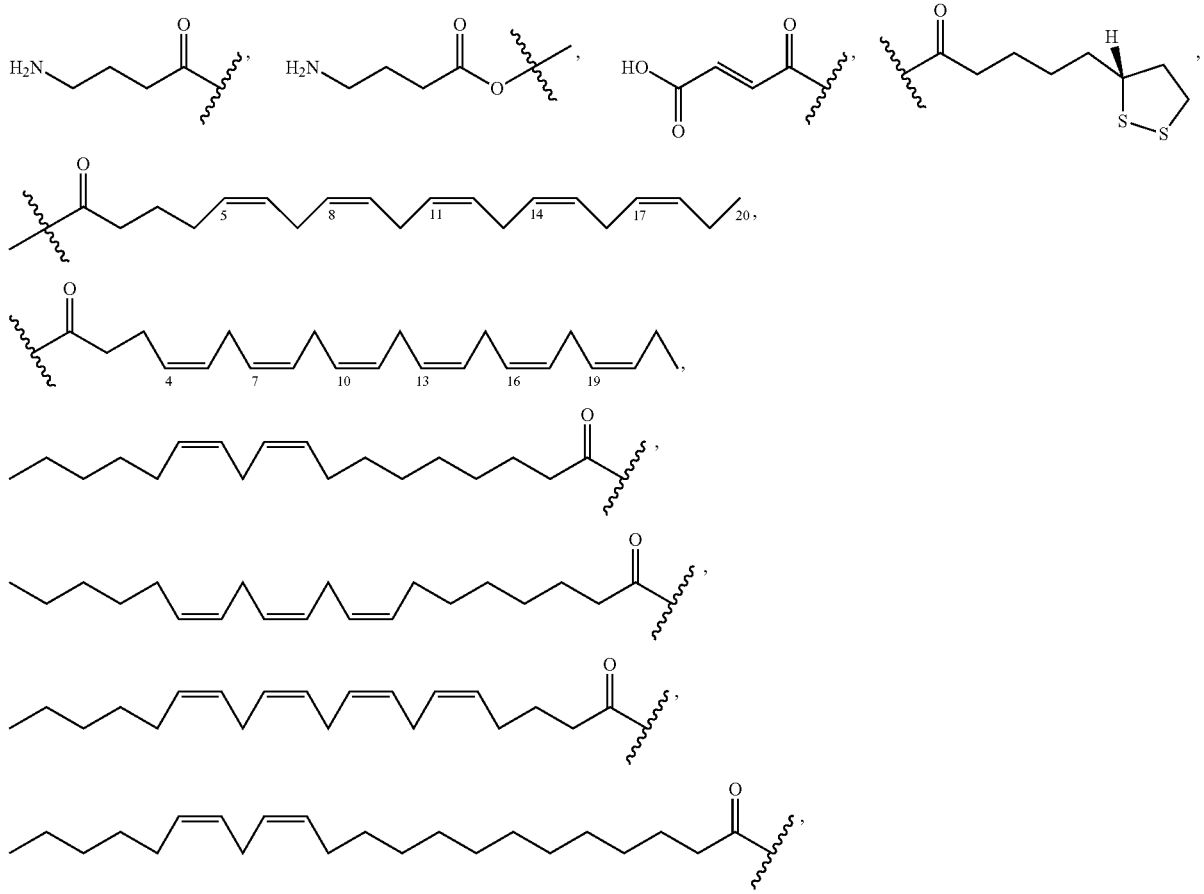

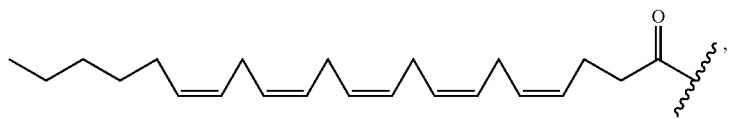
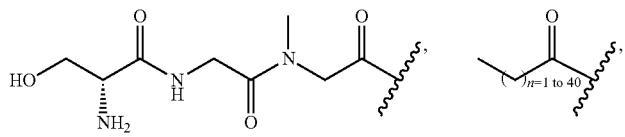
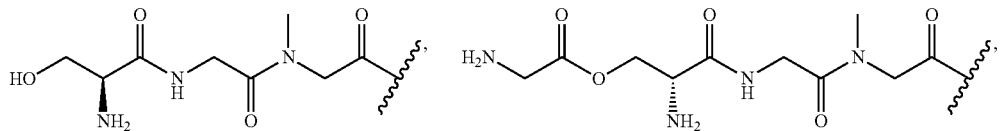
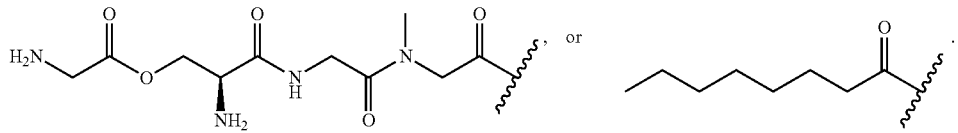
In certain embodiments, the compound of formula I or II is selected from the group:
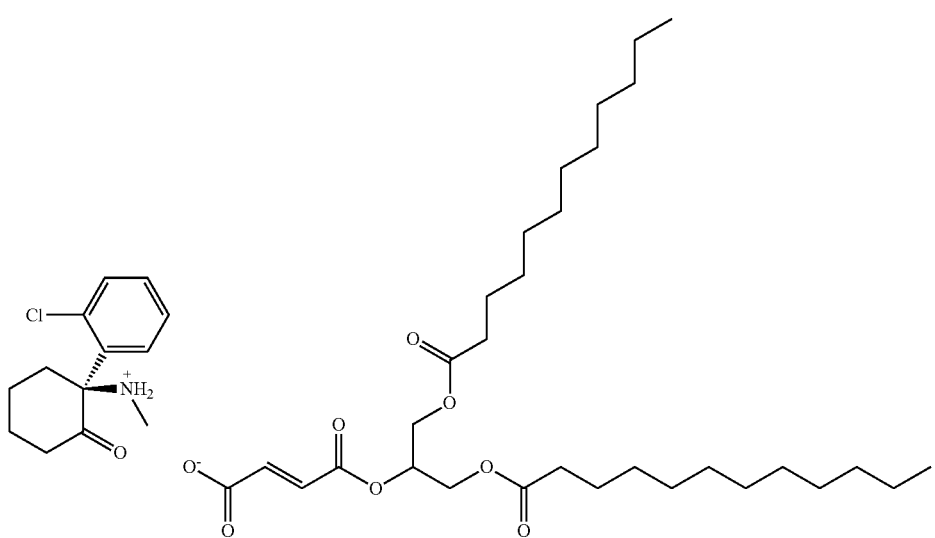
19

-continued
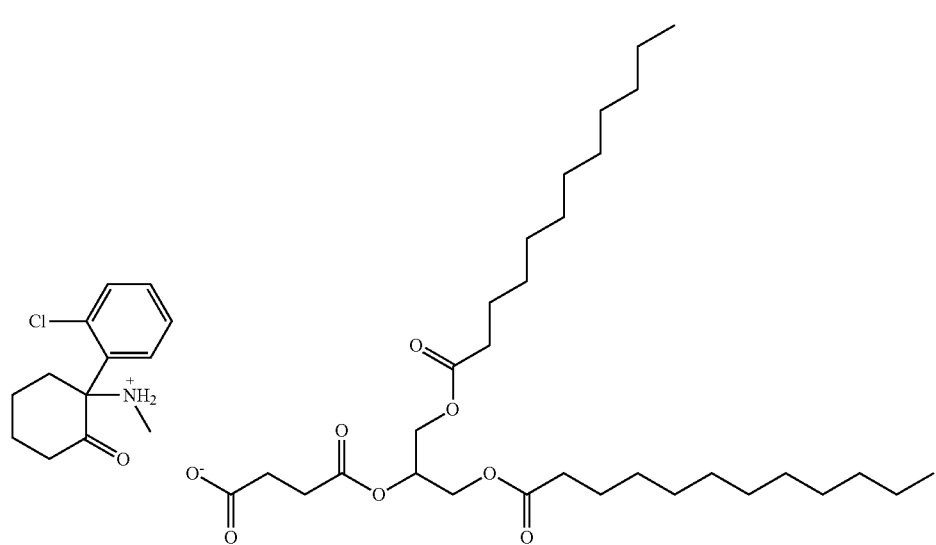
16
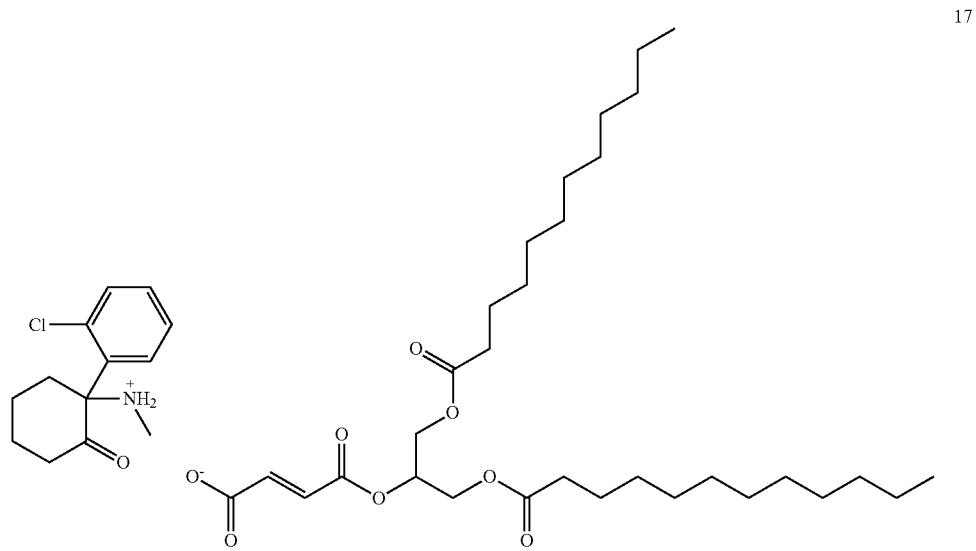
17
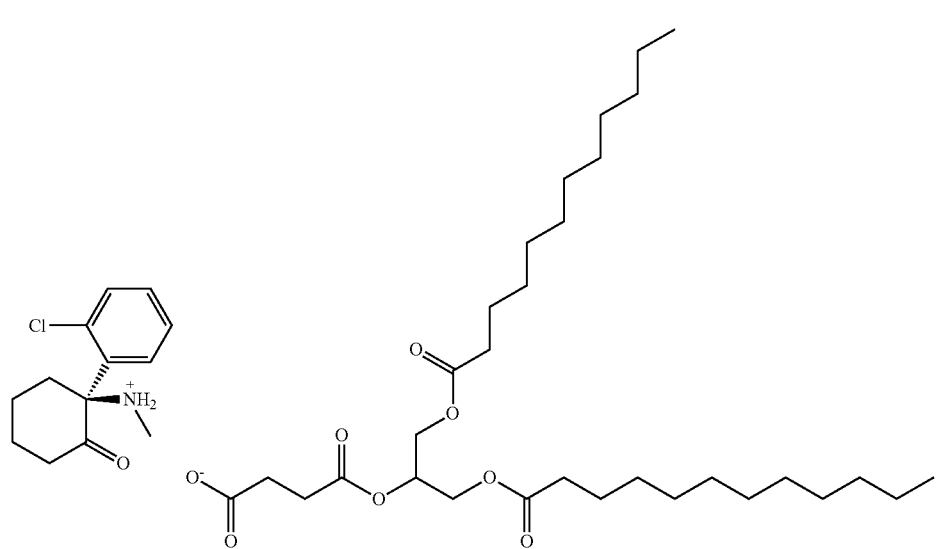
18

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus, it is intended that the present disclosure include such modifications and variations and their equivalents.

EXAMPLES

The disclosure will now be illustrated with working examples, which are intended to illustrate the working of disclosure and not intended to take restrictively to imply any limitations on the scope of the present disclosure.

Methods of Synthesis

Example 1

General Scheme for Acid Part (6) Synthesis

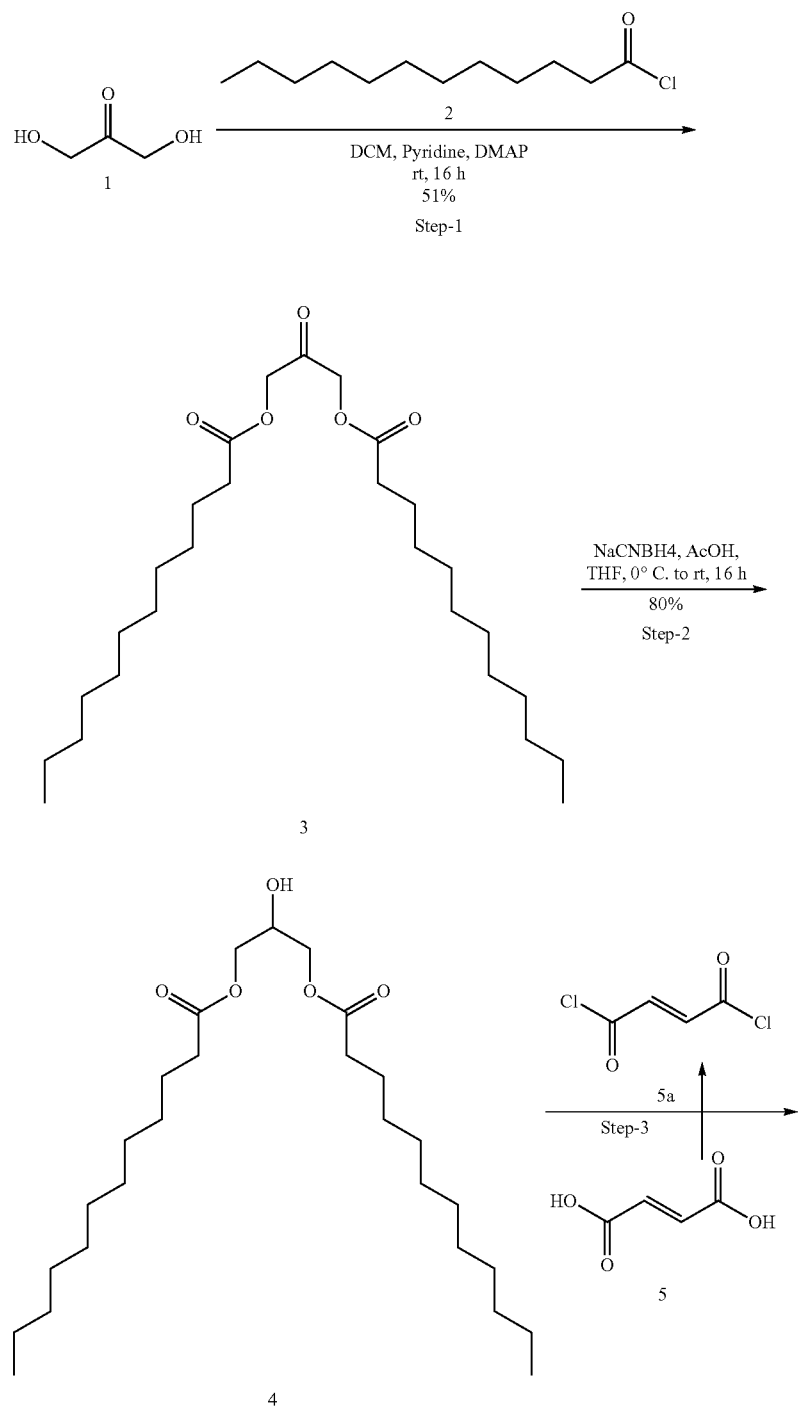

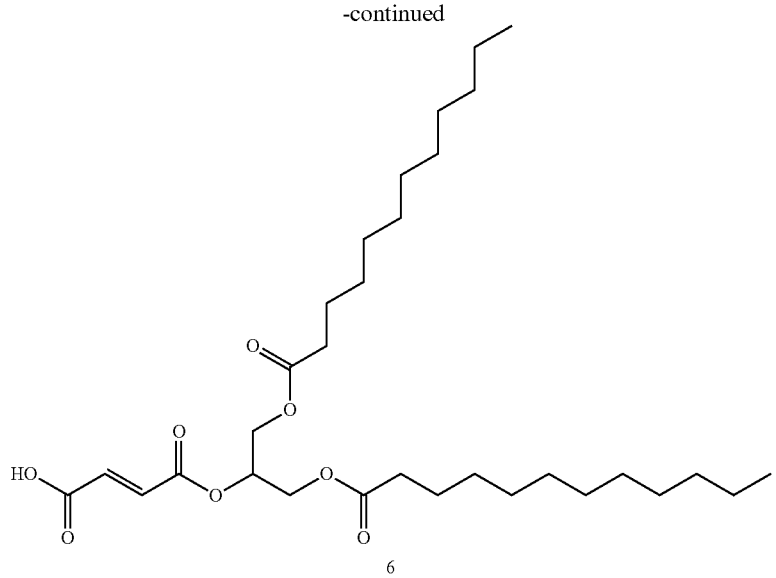

Step-1

Synthesis of 2-oxopropane-1,3-diyl didodecanoate (3)

To an ice cold solution of 1,3-dihydroxypropan-2-one 1 (30.0 g, 0.33 mol) in DCM (500 mL) was added 4-dimethylaminopyridine (20.30 g, 0.167 mol) and pyridine (107 mL, 0.1.332 mol) and stirred for next 5 min. To the above reaction mixture dodecanoyl chloride 2 (218.50 g, 1.167 mol) was added drop wise at 0° C. and the reaction mixture was stirred at room temperature for 16 h. After completion, reaction mixture was filtered, the solid was washed with dichloromethane (100 mL), filtrate was washed with brine (200 mL), saturated solution of sodium bicarbonate (200 mL) and 0.1 N HCl solution (100 mL). The organic layer was separated, dried over anhydrous sodium sulfate and solvent was removed under reduced pressure to get crude. The crude was triturated with diethyl ether to afford the desired product 3 as white solid. Yield: 78 g, 51%.

MS (ESI) m/z 455.37[M+1]+;

$^1$H NMR (400 MHz, DMSO-d$_6$): δ 4.74 (s, 4H), 2.43 (m, 4H), 1.64 (m, 4H), 1.55-1.25 (m, 32H), 0.87 (m, 6H).

Step-2

Synthesis of 2-hydroxypropane-1,3-diyl didodecanoate (4)

To an ice cold solution of 2-oxopropane-1,3-diyl didodecanoate 3 (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4 as white solid. Yield: 60.0 g, 80%.

MS (ESI) m/z 457.48[M+1]+;

$^1$H NMR (400 MHz, DMSO-d$_6$): δ 5.26 (d, J=5.2 Hz, 1H), 3.92-3.98 (m, 4H), 2.28 (m, 4H), 1.50 (m, 4H), 1.23 (m, 33H) and 0.83 (m, 6H).

Step-3

Synthesis of (E)-4-((1,3-bis(dodecanoyloxy)propan-2-yl)oxy)-4-oxobut-2-enoic acid (6)

To an ice-cold solution of fumaric acid 5 (25 g, 215.51 mmol) in DCM (200 mL) was added oxalyl chloride (36.9 mL 431.02 mmol) and DMF in catalytic amount. The resulting reaction mixture was stirred at RT for 4 h. After completion of reaction (TLC monitoring), the reaction mixture was concentrated under reduced pressure to get crude compound 5a (quantitative yield) and used as such without delay.

In another RB flask, to an ice-cold solution of 2-hydroxypropane-1,3-diyl didodecanoate 4 (10.0 g, 21.91 mmol) in DCM (100 mL) was added Et$_3$N (15.19 mL, 109.55 mmol) followed by slow addition of above prepared compound 5a in DCM (20 mL). The resulting mixture was stirred at RT for 16 h. After completion of reaction (TLC monitoring), reaction mixture was concentrated under reduced pressure. The crude was diluted with water (200 mL), adjust pH ~2-3 using 1N—HCl and extracted with dichloromethane (3×200 mL). The organic layer was separated, dried over anhydrous sodium sulfate and concentrated under reduced pressure. The crude thus obtained was purified over silica gel (100-200 mesh) column chromatography eluting with 80% ethyl acetate in hexanes to afford the desired product 6 as white solid. Yield: 2.5 g, 21%.

LC-MS: m/z 553.64[M−1]; 99.63% purity.

$^1$H NMR (400 MHz, DMSO-d$_6$): δ 13.26 (brs, 1H), 6.61 (d, J=15.6 Hz, 2H), 5.29 (m, 1H), 4.29-4.33 (m, 2H), 4.18-4.23 (m, 2H), 2.28 (m, 4H), 1.48 (m, 4H), 1.22 (m, 32H) and 0.83 (m, 6H).

Example 2

General Scheme for Acid Part (8) Synthesis

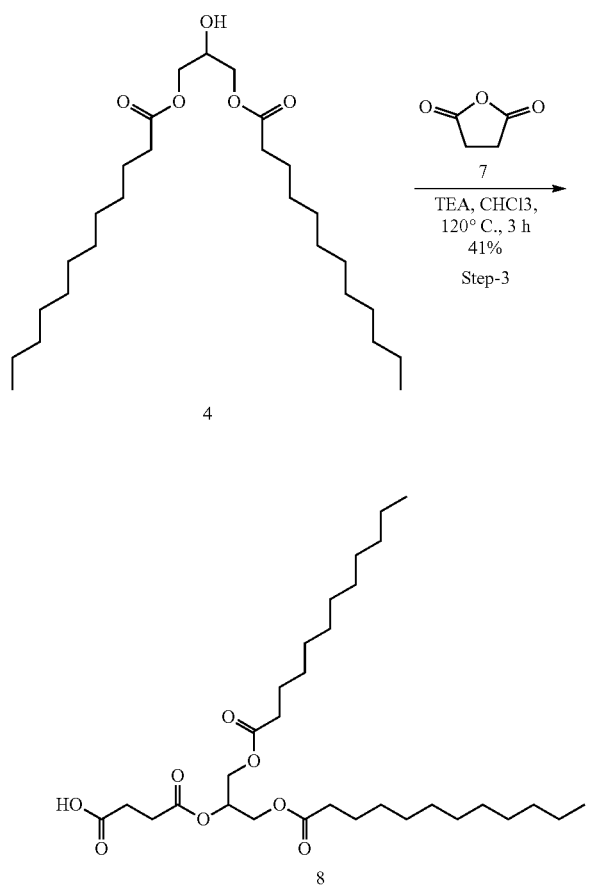

Synthesis of 4-((1,3-bis(dodecanoyloxy)propan-2-yl)oxy)-4-oxobutanoic acid (8)

To a solution of 2-hydroxypropane-1,3-diyl didodecanoate 4 (40.0 g, 0.087 mol) in chloroform (200 mL), dihydrofuran-2,5-dione 5 (10.50 g, 0.105 mol) and triethylamine (18.50 mL, 0.131 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 25 to 30% ethyl acetate in hexanes to afford the desired product 8 as white solid. Yield: 20.0 g, 41%.

MS (ESI) m/z 555.40[M−1];

$^1$H NMR (400 MHz, DMSO-$d_6$): δ 12.30 (s, 1H), 5.17 (m, 1H), 4.18-4.25 (m, 4H), 2.50-2.47 (m, 8H), 1.23-1.25 (m, 36H), 0.83 (m, 6H).

Example 3

General Scheme for Esketamine (15) Synthesis

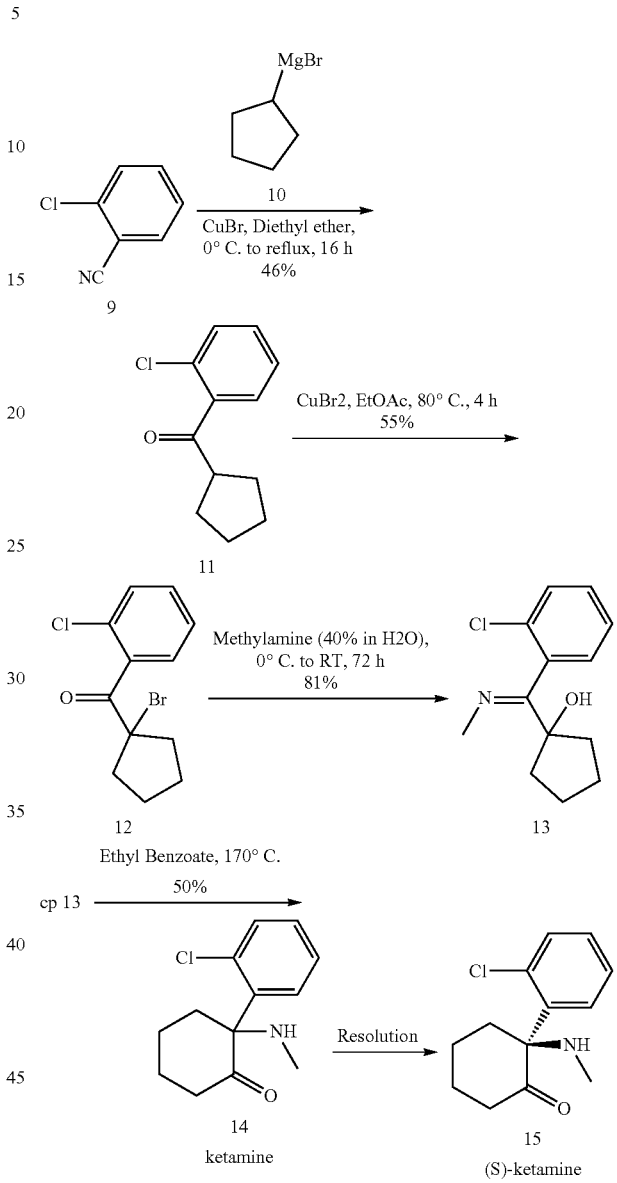

Synthesis of (2-chlorophenyl)(cyclopentyl)methanone (11)

To an ice cold solution of 2-chlorobenzonitrile 9 (100 g, 0.73 mol) in diethyl ether (800 mL) was added copper(I) bromide (5.20 g, 0.037 mol) followed by the addition of cyclopentylmagnesium bromide 10 (438 mL, 0.88 mol, 2.0M in diethyl ether) in drop-wise manner. The resulting reaction mass was heated up to 50° C. and maintained the temperature for next 16 h. After completion of reaction (TLC monitoring), the reaction mass was quenched with 6N HCl (500 mL) and biphasic layer was separated. The aqueous layer was extracted by diethyl ether (2×500 mL). Combined organics were washed with brine solution, dried over anhydrous Na2SO4, filtered and solvent was evaporated under reduced pressure to get the crude product as brown sticky liquid. The crude thus obtained was purified by silica gel (100-200 mesh) column chromatography eluting with 3 to 5% ethyl acetate in hexanes to afford the desired product 11 as light brown liquid. Yield: 70.0 g, 46%.

MS (ESI) m/z 207.01[M−1];

$^1$H NMR (400 MHz, DMSO-$d_6$): δ 7.63-7.40 (m, 4H), 3.54 (m, 1H), 1.65 (m, 4H) and 1.58 (m, 4H).

Synthesis of (1-bromocyclopentyl)(2-chlorophenyl)methanone (12)

To an ice cold solution of (2-chlorophenyl)(cyclopentyl)methanone 11 (40 g, 0.19 mol) in EtOAc (400 mL) was added CuBr$_2$ (128 g, 0.58 mol) portion wise. The resulting reaction mass was heated up to 80° C. and maintained the temperature for next 3 h. After completion of reaction (TLC monitoring), the reaction mass cooled up to 5° C. and during this time solid precipitated out in reaction mass. Solid thus obtained was filtered and the mother liquid was evaporated under reduced pressure. The crude thus obtained was dissolved in DCM (250 mL) and it was cooled again up to 0° C. for 30 minutes resulting in solid precipitation, which was filtered. The solid was discarded and the DCM filtrate was concentrated under reduced pressure to afford the crude material as brown viscous liquid which was carried forward for the next step without further purification.

Yield: 30.0 g, 55%.

MS (ESI) m/z 284.31[M−1]; $^1$H NMR (400 MHz, CDCl$_3$): δ 7.70 (m, 1H), 7.42-7.40 (m, 1H), 7.37-7.33 (m, 1H), 7.27 (m, 1H), 2.36 (m, 4H), 2.08 (m, 2H) and 1.85 (m, 2H).

Synthesis of 1-((2-chlorophenyl)(methylimino)methyl)cyclopentan-1-ol (13)

A solution of (1-bromocyclopentyl)(2-chlorophenyl)methanone 12 (30 g, 0.10 mol) in 40% Aq. soln. of methyl amine (150 mL) was stirred at room temperature for next 72 h. After completion of reaction (TLC monitoring), compound was extracted with diethyl ether (2×250 mL). Combined organics were washed with brine solution, dried over anhydrous Na$_2$SO$_4$, filtered and solvent was evaporated under reduced pressure to get the crude product as brown sticky liquid. The crude thus obtained was purified by basic alumina column chromatography eluting with 5 to 10% ethyl acetate in hexanes to afford the desired product 13 as light brown liquid. Yield: 22.0 g, 81%.

LC-MS: m/z 238.18[M+1]; 99.42% purity.

$^1$H NMR (400 MHz, DMSO-$d_6$): δ 7.59 (m, 1H), 7.34 (m, 2H), 7.21 (m, 1H), 2.84 (br, s, 1H), 2.49 (m, 2H), 2.31 (m, 2H), 1.94 (s, 3H), 1.87 (m, 2H) and 1.71-1.61 (m, 2H).

Synthesis of 2-(2-chlorophenyl)-2-(methylamino)cyclohexan-1-one (14)

To an ice cold solution of 1-((2-chlorophenyl)(methylimino)methyl)cyclopentan-1-ol 13 (12.0 g, 0.05 mol) in diethyl ether (100 mL) was added 3M HCl in cyclopentyl methyl ether (CPME) (100 mL). The resulting reaction mixture was stirred at room temperature for next 30 min. After salt formation, solvent was evaporated under reduced pressure to afford the crude as sticky solid. The resulting crude material was taken in ethyl benzoate (75 mL) and heated it up to 170° C. for 4 h. After completion of reaction (TLC monitoring), resulting reaction mass was cooled up to room temperature and added on hexane (750 mL). Solid thus precipitated was filtered and washed with hexane to afford the desired product 14 as light brown solid.

Yield: 6.0 g, 50%. LC-MS: m/z 238.18[M+1]; 99.43% purity.

$^1$H NMR (400 MHz, DMSO-$d_6$): 7.59 (m, 1H), 7.38 (m, 2H), 7.29 (m, 1H), 2.84 (br, s, 1H), 2.49 (m, 2H), 2.31 (m, 2H), 1.94 (s, 3H), 1.87 (m, 2H) and 1.71-1.61 (m, 2H).

From (2-(2-chlorophenyl)-2-(methylamino)cyclohexan-1-one) (14), (S)-2-(2-chlorophenyl)-2-(methylamino)cyclohexan-1-one (15) was isolated by using normal phase Chiral prep (Chiral Cell OJH, 0.1% DEA in hexane, 90:10, Flow rate, 23 mL/min).

Example 4

Synthesis of (E)-4-((1,3-bis(dodecanoyloxy)propan-2-yl)oxy)-4-oxobut-2-enoate (S)-1-(2-chlorophenyl)-N-methyl-2-oxocyclohexan-1-aminium (19)

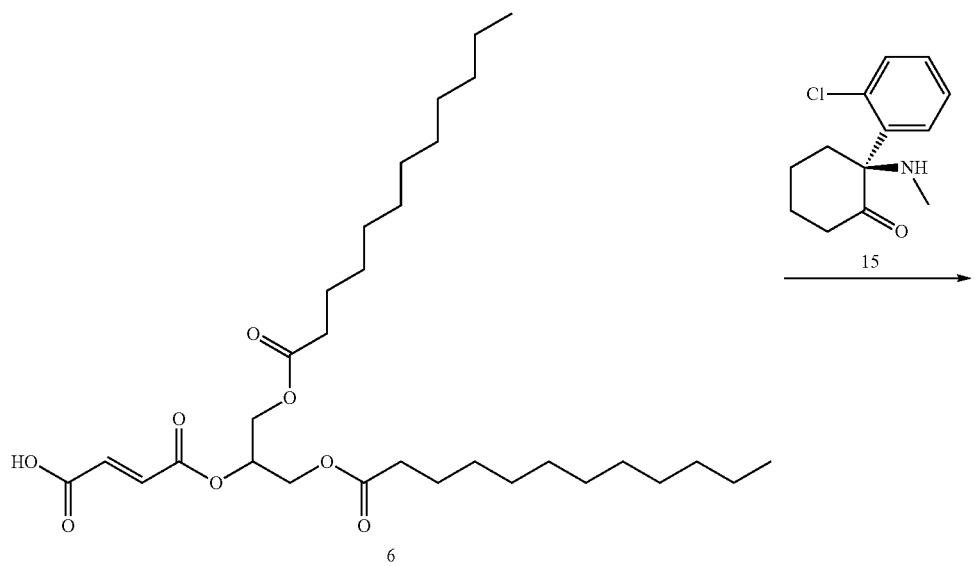

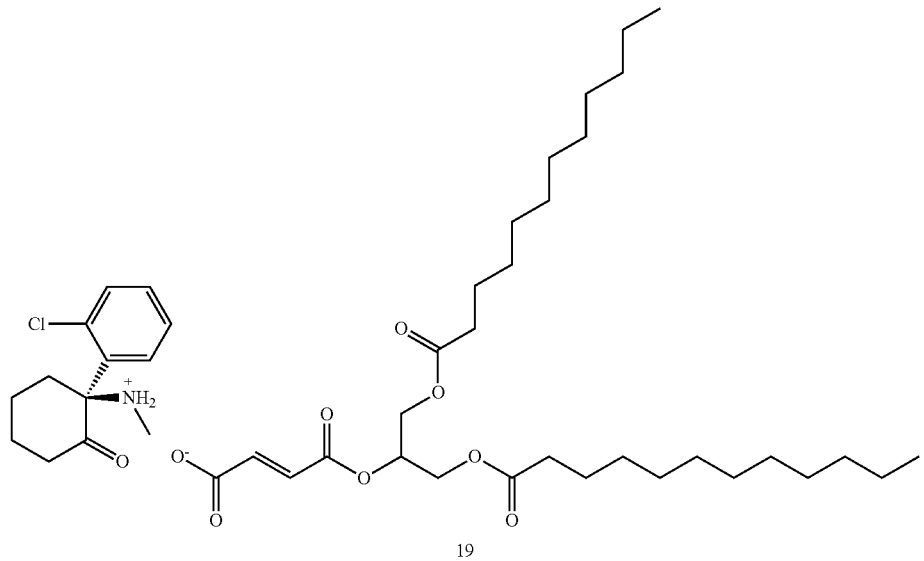

To a solution of (E)-4-((1,3-bis(dodecanoyloxy)propan-2-yl)oxy)-4-oxobut-2-enoate 6 (2.0 g, 3.61 mmol) in acetonitrile (25 mL) was added (S)-2-(2-chlorophenyl)-2-(methylamino)cyclohexan-1-one 15 (0.86 g, 3.61 mmol) at ambient temperature. The resulting reaction mixture was heated up to 50° C. for next 3 h followed by the evaporation of solvent under reduced pressure to get the desired product 19 as off-white solid Yield: 2.86 g, quantitative Example 5

Synthesis of 4-((1,3-bis(dodecanoyloxy)propan-2-yl)oxy)-4-oxobutanoate 1-(2-chlorophenyl)-N-methyl-2-oxocyclohexan-1-aminium (16)

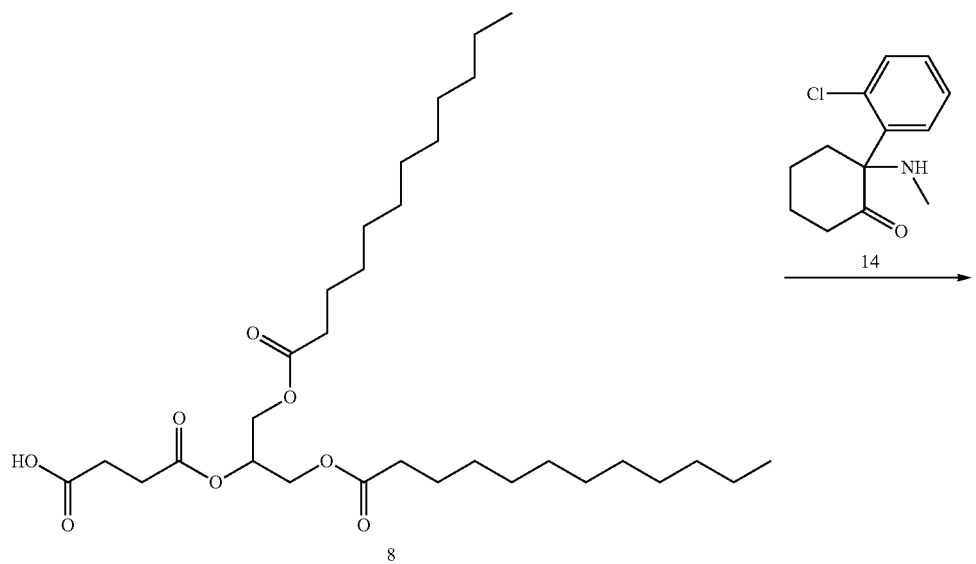

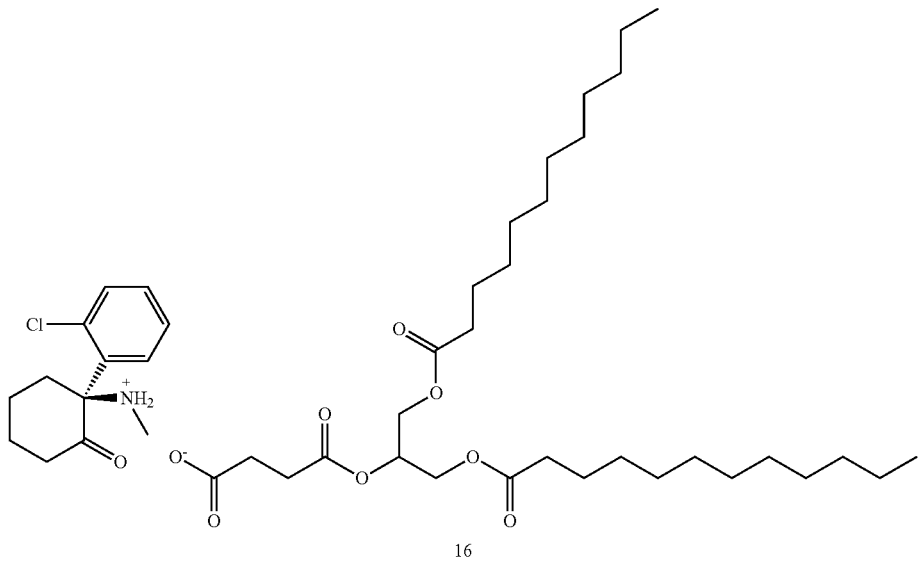

16

To a solution of 4-((1,3-bis(dodecanoyloxy)propan-2-yl)oxy)-4-oxobutanoic acid 8 (2.20 g, 3.95 mmol) in acetonitrile (25 mL) was added 2-(2-chlorophenyl)-2-(methylamino)cyclohexan-1-one 14 (0.94 g, 3.95 mmol) at ambient temperature. The resulting reaction mixture was heated up to 50° C. for next 3 h followed by the evaporation of solvent under reduced pressure to get the desired product 16 as off-white solid Yield. 3.14 g, quantitative.

Example 6

Synthesis of (E)-4-((1,3-bis(dodecanoyloxy)propan-2-yl)oxy)-4-oxobut-2-enoate 1-(2-chlorophenyl)-N-methyl-2-oxocyclohexan-1-aminium (17)

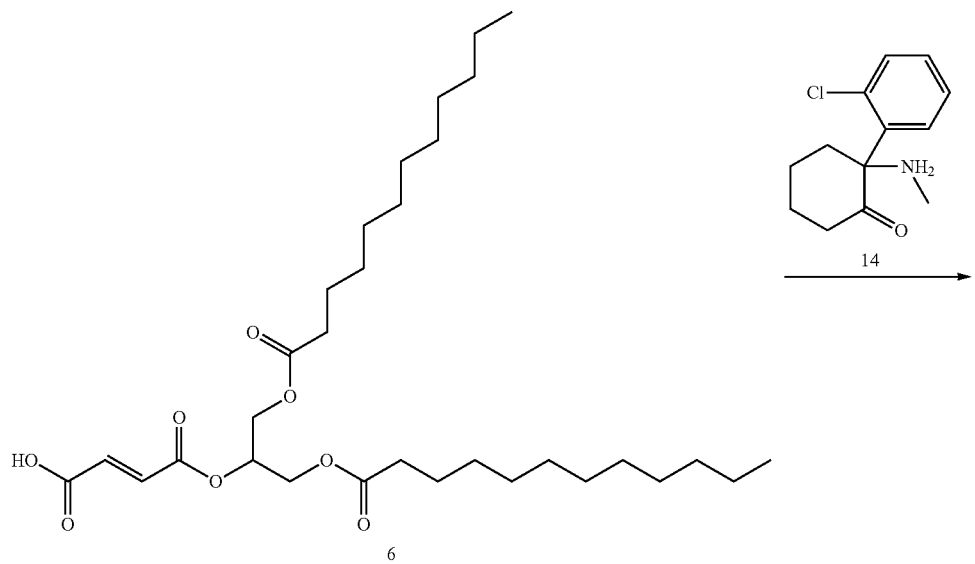

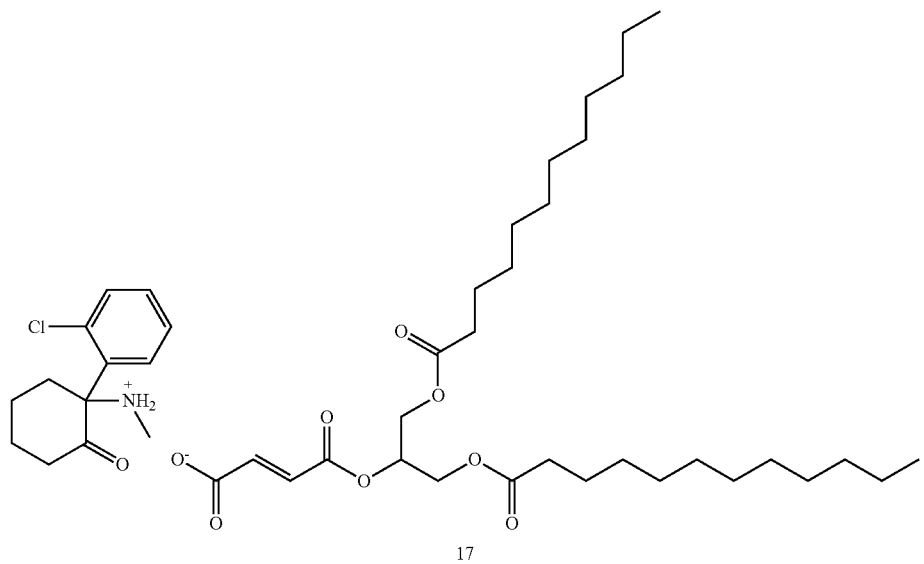

To a solution of (E)-4-((1,3-bis(dodecanoyloxy)propan-2-yl)oxy)-4-oxobut-2-enoate 6 (2.20 g, 3.97 mmol) in acetonitrile (25 mL) was added 2-(2-chlorophenyl)-2-(methylamino)cyclohexan-1-one 14 (0.943 g, 3.97 mmol) at ambient temperature. The resulting reaction mixture was heated up to 50° C. followed by the evaporation of solvent under reduced pressure to get the desired product 17 as off-white solid Yield: 3.13 g, quantitative Example 7

Synthesis of 4-((1,3-bis(dodecanoyloxy)propan-2-yl)oxy)-4-oxobutanoate (S)-1-(2-chlorophenyl)-N-methyl-2-oxocyclohexan-1-aminium (18)

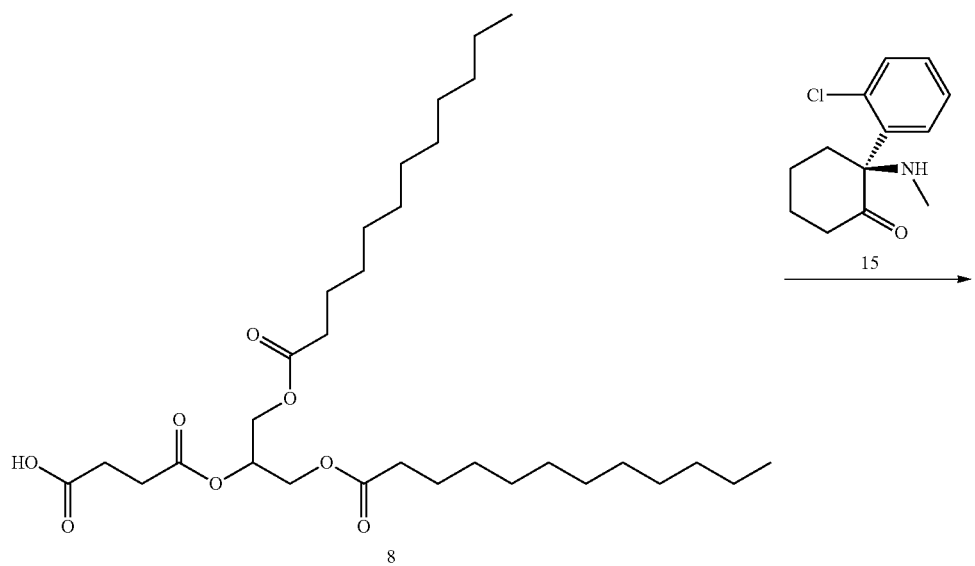

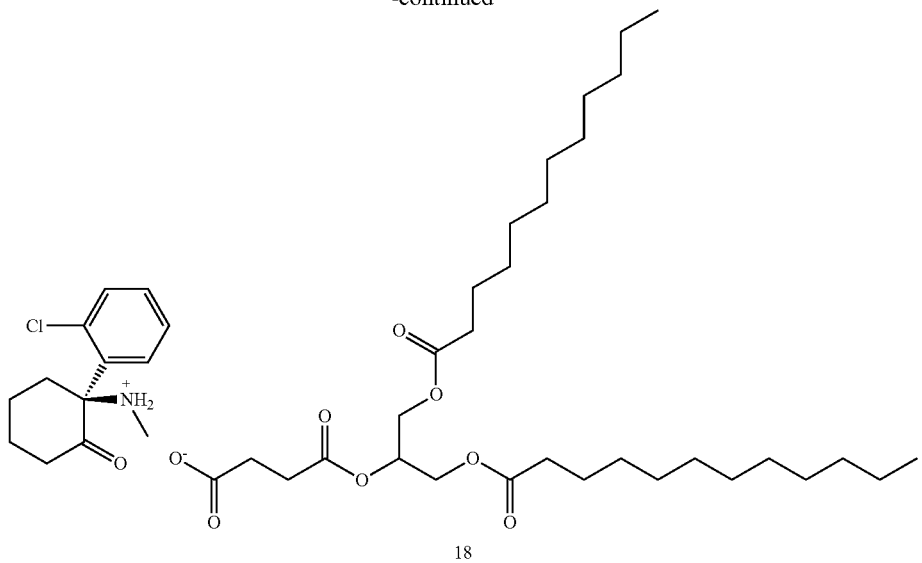

18

To a solution of 4-((1,3-bis(dodecanoyloxy)propan-2-yl)oxy)-4-oxobutanoic acid 8 (2.20 g, 3.95 mmol) in acetonitrile (25 mL) was added (S)-2-(2-chlorophenyl)-2-(methylamino)cyclohexan-1-one 15 (0.94 g, 3.95 mmol) at ambient temperature. The resulting reaction mixture was heated up to 50° C. for next 3 h followed by the evaporation of solvent under reduced pressure to get the desired product 18 as off-white solid.

Yield: 3.14 g, quantitative.

I claim:
1. A compound of Formula I

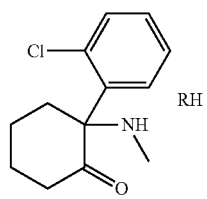

Formula I wherein
RH is caprylic acid, adipic acid, capric acid, caproic acid, cinnamic acid, cyclamic acid, dodecylsulfuric acid, galactaric acid, gentisic acid, glucuronic acid, glutaric acid, glycerophosphoric acid, malonic acid, nicotinic acid, oleic acid, oxalic acid, palmitic acid, sebacic acid, omega 3 fatty acids, omega 6 fatty acids, n-acetyl cysteine, caprilic acid, alpha lipoic acid, R-lipoic acid, myristic acid, myristoleic acid, palmitoleic acid, phospholipids, phosphatidylcholine, elaidic acid, linoleic acid, linolenic acid, menthol, retinoic acid, vitamin A, retinol, linolelaidic acid, arachidonic acid, retinal, isotretinoin, curcumin, tretinoin, α-carotene, β-carotene, d2 ergosterol, ergocalciferol, 7-dehydrocholesterol, cholecalciferol, 25-hydroxycholecalciferol, calcitriol (1,25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone, menaquinones, menadione, menadiol, thiamine, acefurtiamine, allithiamine, benfotiamine, fursultiamine, octotiamine, prosultiamine, sulbutiamine, riboflavin, niacin, nicotinamide, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, dehydroascorbic acid, 1-docosanol or

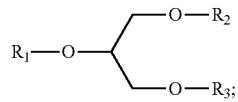

wherein, each of $R_1$, $R_2$ and $R_3$ is independently

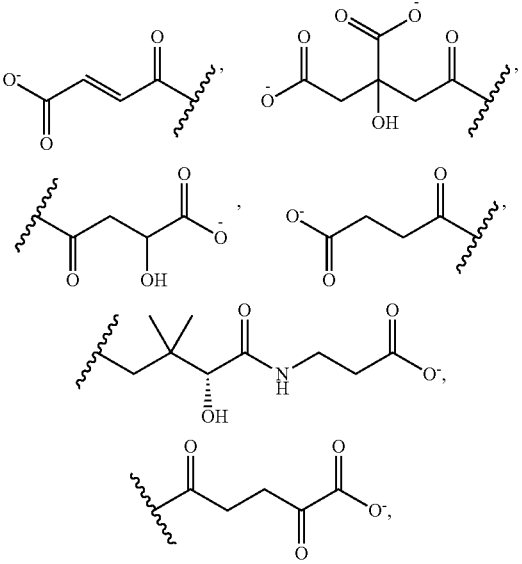

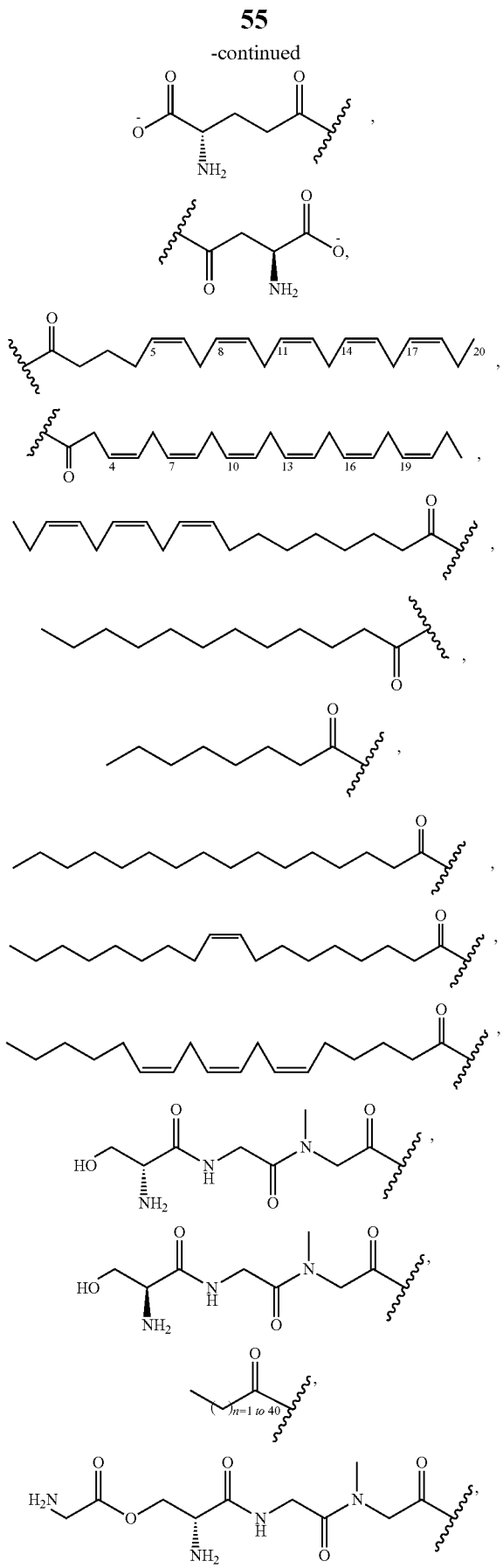

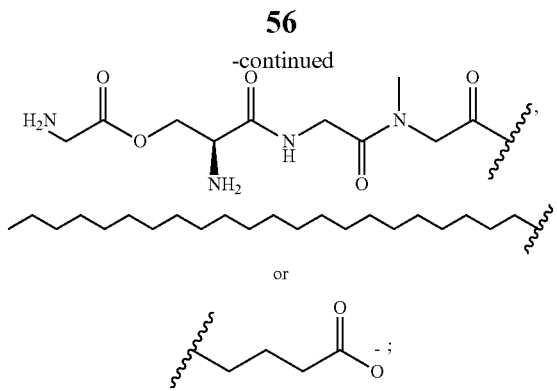

or a pharmaceutically acceptable hydrate, solvate, enantiomer, and stereoisomer thereof.

2. A compound of Formula II

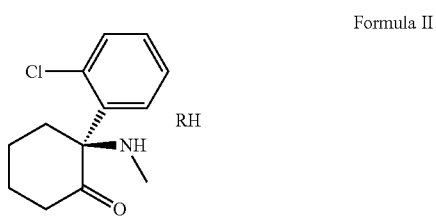

wherein

RH is caprylic acid, adipic acid, capric acid, caproic acid, cinnamic acid, cyclamic acid, dodecylsulfuric acid, galactaric acid, gentisic acid, glucuronic acid, glutaric acid, glycerophosphoric acid, malonic acid, nicotinic acid, oleic acid, oxalic acid, palmitic acid, sebacic acid, undecylenic acid, omega 3 fatty acids, omega 6 fatty acids, n-acetyl cysteine caprilic acid, alpha lipoic acid, R-lipoic acid, myristic acid, myristoleic acid, palmitoleic acid, phospholipids, phosphatidylcholine, elaidic acid, linoleic acid, linolenic acid, menthol, retinoic acid, vitamin A, retinol, linolelaidic acid, arachidonic acid, retinal, isotretinoin, curcumin, tretinoin, α-carotene, β-carotene, d2 ergosterol, ergocalciferol, 7-dehydrocholesterol, cholecalciferol, 25-hydroxycholecalciferol, calcitriol (1,25-dihydroxycholecalciferol), calcitroic acid, d4 dihydroergocalciferol, alfacalcidol, dihydrotachysterol, calcipotriol, tacalcitol, paricalcitol, tocopherol, naphthoquinone, phylloquinone, menaquinones, menadione, menadiol, thiamine, acefurtiamine, allithiamine, benfotiamine, fursultiamine, octotiamine, prosultiamine, sulbutiamine, riboflavin, niacin, nicotinamide, dexpanthenol, pantethine, pyridoxine, pyridoxal phosphate, pyridoxamine, pyritinol, biotin, folic acid, dihydrofolic acid, folinic acid, levomefolic acid, adenosylcobalamin, cyanocobalamin, hydroxocobalamin, methylcobalamin, choline, dehydroascorbic acid, 1-docosanol or

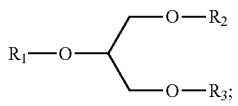

wherein, each of $R_1$, $R_2$ and $R_3$ is independently

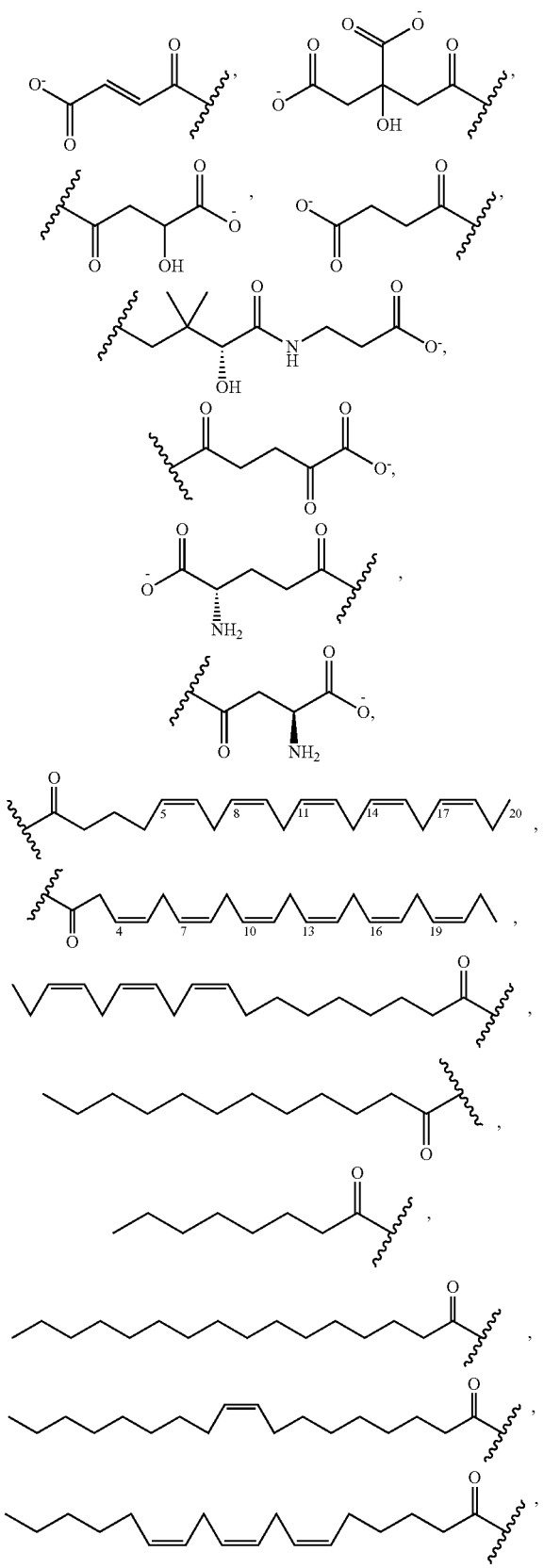

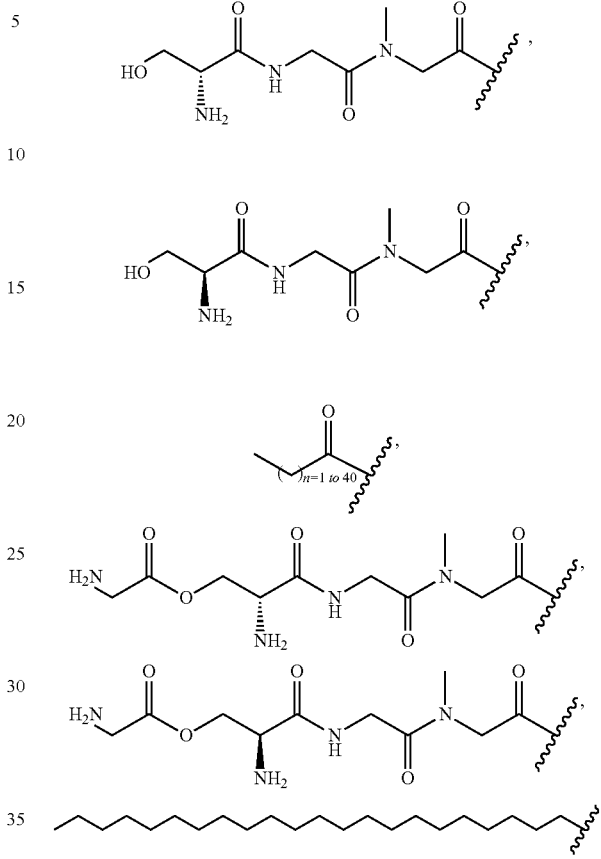

or a pharmaceutically acceptable hydrate, solvate, enantiomer, and stereoisomer thereof.

3. A compound of claim 1, wherein the ketamine moiety in the compound of formula I is selected from an R enantiomer, an S enantiomer, or a racemic mixture comprising equal portions of R and S enantiomers of the ketamine.

4. A compound of claim 2, wherein the ketamine moiety in the compound of formula II is an S-enantiomer of the ketamine.

5. A compound of claim 1, wherein the compound is selected from a group consisting of

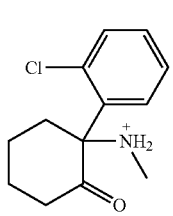

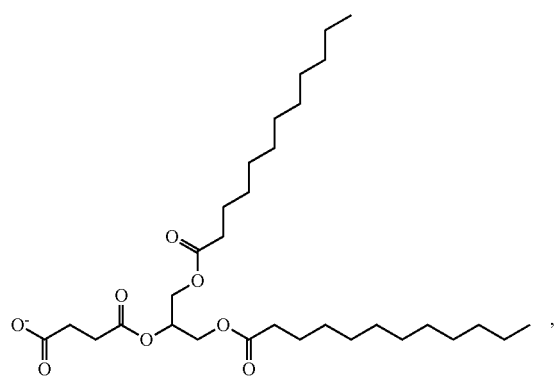

and

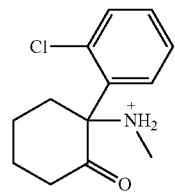

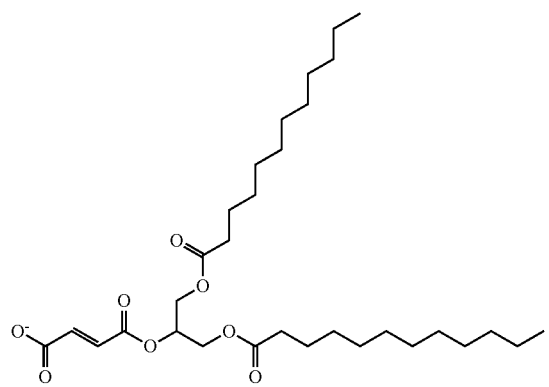

and pharmaceutically acceptable hydrates, solvates, enantiomers, and stereoisomers thereof.

6. A compound of claim 2, wherein the compound is selected from a group consisting of

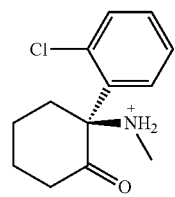

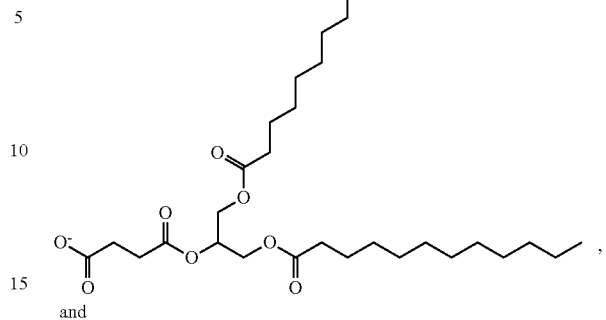

and

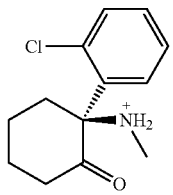

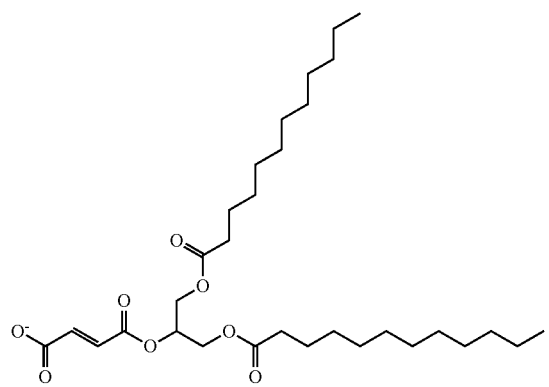

and pharmaceutically acceptable hydrates, solvate, enantiomer, and stereoisomer thereof.

7. A pharmaceutical composition comprising a compound of claim 1 as an active ingredient in a therapeutically effective amount; and a pharmaceutically acceptable excipient and/or pharmaceutically acceptable carrier.

8. The pharmaceutical composition of claim 7, wherein the pharmaceutically acceptable excipient is selected from the group comprising of a stabilizer, an inert carrier, a vehicle, a diluent, a surfactant, a filler, a humectant, an adsorbent, an antiadherent, a binder, a lubricant, a glidant, a super disintegrant, a disintegrant, a preservative, an antioxidant, a solution retarding agent, an absorption accelerator, a wetting agent, an absorbent, a coloring agent, a flavoring agent, a sorbent, a coating agent, a sweetener, a buffering agent, a propellant, and mixtures thereof.

9. The pharmaceutical composition of claim 7, wherein the pharmaceutical composition is formulated as an oral dosage form, systemic dosage form, topical dosage form, spray, parenteral dosage form, subdermal dosage form, or transdermal dosage form.

10. The pharmaceutical composition of claim 7, wherein the pharmaceutical composition is formulated in a unit dosage form selected from the group consisting of tablet, sublingual tablet, mucoadhesive tablet, multilayer tablet, capsule, capsules containing tablet, controlled-release form, sustained-release form, suppository, tampons, pessaries, pill, lozenge, powder, beads, granule, nanoparticles, beads or granules in solid or liquid forms, oral spray, nasal spray, mucoadhesive spray, intra nasal spray, foam, nasal inhaler, liquid solution, syrups, elixirs, emulsions, microemulsions, subdermal autoinjector, intramuscular autoinjector, injection, stereotactic injection, liquid suspension, intravenous suspension, sterile parenteral solution, sterile parenteral suspension, sterile non-parenteral solution, sterile non-parenteral suspension, topical ointment, topical paste, topical cream, topical lotion, topical gel, and transdermal patch.

11. A method of the treatment or amelioration of neurological diseases or an associated complication, wherein the associated complication is selected from the group consisting of depression, treatment resistant depression, chronic pain and combinations thereof, and comprising administering to a patient suffering from neurological diseases or associated complications the compound of claim 1 as an active ingredient in a therapeutically effective amount, or the pharmaceutical composition of claim 7.

12. A kit comprising a compound of claim 1 as an active ingredient in a therapeutically effective amount, and an instruction for use in the treatment of neurological diseases and associated complications wherein the associated complications are selected from the group consisting of depression, treatment resistant depression, chronic pain and combinations thereof.

13. A kit comprising a pharmaceutical composition of claim 7, and an instruction for use in the treatment of neurological diseases and associated complications wherein the associated complications are selected from the group consisting of depression, treatment resistant depression, chronic pain and combinations thereof.

14. The pharmaceutical compositions of claim 10, wherein said pharmaceutical compositions are formulated for the treatment of a neurological diseases or an associated complication wherein the associated complication is selected from the group consisting of depression, treatment resistant depression, chronic pain and combinations thereof.

15. A pharmaceutical composition comprising a compound of claim 2 as an active ingredient in a therapeutically effective amount; and a pharmaceutically acceptable excipient and/or pharmaceutically acceptable carrier.

16. The pharmaceutical composition of claim 15, wherein the pharmaceutically acceptable excipient is selected from the group comprising of a stabilizer, an inert carrier, a vehicle, a diluent, a surfactant, a filler, a humectant, an adsorbent, an antiadherent, a binder, a lubricant, a glidant, a super disintegrant, a disintegrant, a preservative, an antioxidant, a solution retarding agent, an absorption accelerator, a wetting agent, an absorbent, a coloring agent, a flavoring agent, a sorbent, a coating agent, a sweetener, a buffering agent, a propellant, and mixtures thereof.

17. The pharmaceutical composition of claim 15, wherein the pharmaceutical composition is formulated as an oral dosage form, systemic dosage form, topical dosage form, spray, parenteral dosage form, subdermal dosage form, or transdermal dosage form.

18. The pharmaceutical composition of claim 15, wherein the pharmaceutical composition is formulated in a unit dosage form selected from the group consisting of tablet, sublingual tablet, mucoadhesive tablet, multilayer tablet, capsule, capsules containing tablet, controlled-release form, sustained-release form, suppository, tampons, pessaries, pill, lozenge, powder, beads, granule, nanoparticles, beads or granules in solid or liquid forms, oral spray, nasal spray, mucoadhesive spray, intra nasal spray, foam, nasal inhaler, liquid solution, syrups, elixirs, emulsions, microemulsions, subdermal autoinjector, intramuscular autoinjector, injection, stereotactic injection, liquid suspension, intravenous suspension, sterile parenteral solution, sterile parenteral suspension, sterile non-parenteral solution, sterile non-parenteral suspension, topical ointment, topical paste, topical cream, topical lotion, topical gel, and transdermal patch.

19. A method of the treatment or amelioration of neurological diseases or an associated complication, wherein the associated complication is selected from the group consisting of depression, treatment resistant depression, chronic pain and combinations thereof, and comprising administering to a patient suffering from neurological diseases or associated complications the compound of claim 2 as an active ingredient in a therapeutically effective amount, or the pharmaceutical composition of claim 15.

20. A kit comprising a compound of claim 2 as an active ingredient in a therapeutically effective amount, and an instruction for use in the treatment of neurological diseases and associated complications wherein the associated complications are selected from the group consisting of depression, treatment resistant depression, chronic pain and combinations thereof.

21. The pharmaceutical compositions of claim 18, wherein said pharmaceutical compositions are formulated for the treatment of neurological diseases or an associated complication wherein the associated complication is selected from the group consisting of depression, treatment resistant depression, chronic pain and combinations thereof.

* * * * *